(12) United States Patent
Biester et al.

(10) Patent No.: US 12,329,416 B2
(45) Date of Patent: *Jun. 17, 2025

(54) REAMER INSTRUMENTS AND RELATED METHODS

(71) Applicant: Medos International Sarl, Le Locle (CH)

(72) Inventors: Eric Biester, Barrington, RI (US); Cory Emil, Milton, MA (US); Michael Sorrenti, Middleboro, MA (US); Richard W. Fournier, New Bedford, MA (US); Ralph Solitario, Pocasset, MA (US)

(73) Assignee: Medos International Sàrl, Le Locle (CH)

( * ) Notice: Subject to any disclaimer, the term of this patent is extended or adjusted under 35 U.S.C. 154(b) by 166 days.

This patent is subject to a terminal disclaimer.

(21) Appl. No.: 18/126,253

(22) Filed: Mar. 24, 2023

(65) Prior Publication Data
US 2023/0248394 A1  Aug. 10, 2023

Related U.S. Application Data

(63) Continuation of application No. 17/069,626, filed on Oct. 13, 2020, now Pat. No. 11,638,596, which is a
(Continued)

(51) Int. Cl.
*A61B 17/68* (2006.01)
*A61B 17/16* (2006.01)
*A61B 17/70* (2006.01)

(52) U.S. Cl.
CPC ........ *A61B 17/686* (2013.01); *A61B 17/1635* (2013.01); *A61B 17/1671* (2013.01); *A61B 17/7037* (2013.01); *A61B 17/7076* (2013.01)

(58) Field of Classification Search
CPC ....... A61B 17/68; A61B 17/686; A61B 17/16; A61B 17/1635; A61B 17/1671; A61B 17/70; A61B 17/7037; A61B 17/7076
See application file for complete search history.

(56) References Cited

U.S. PATENT DOCUMENTS 5,810,828 A  9/1998  Lightman et al.
5,993,453 A  11/1999  Bullara et al.
(Continued)

FOREIGN PATENT DOCUMENTS

WO  2011068516 A1  6/2011
WO  2016149635 A1  9/2016

OTHER PUBLICATIONS

International Search Report and Written Opinion for Application No. PCT/IB2019/058875, mailed Jan. 15, 2021.
(Continued)

*Primary Examiner* — Christopher J Beccia
(74) *Attorney, Agent, or Firm* — Barnes & Thornburg LLP

(57) ABSTRACT

Reamer instruments and related methods are disclosed herein, e.g., for reaming bone to facilitate in situ assembly of a bone anchor. In some embodiments, the instrument can include a feedback mechanism configured to alert the user when sufficient bone has been removed to facilitate assembly of the bone anchor. The feedback mechanism can be triggered by a movable shaft of the instrument that is displaced by the shank portion of the bone anchor as the surrounding bone is reamed.

23 Claims, 24 Drawing Sheets

Related U.S. Application Data continuation of application No. 16/164,532, filed on Oct. 18, 2018, now Pat. No. 10,835,289.

(56) References Cited

U.S. PATENT DOCUMENTS

| | | | |
|---|---|---|---|
| 6,015,411 A * | 1/2000 | Ohkoshi | A61B 17/16 |
| | | | 279/93 |
| 6,228,058 B1 | 5/2001 | Dennis et al. | |
| 6,443,956 B1 | 9/2002 | Ray | |
| 8,029,509 B2 | 10/2011 | Ducharme | |
| 8,062,319 B2 | 11/2011 | Philip | |
| 8,152,808 B2 | 4/2012 | Steiner et al. | |
| 8,394,109 B2 | 3/2013 | Hutton et al. | |
| 8,469,960 B2 | 6/2013 | Hutton et al. | |
| 8,486,074 B2 | 7/2013 | Steiner et al. | |
| 8,882,661 B2 | 11/2014 | Hutton et al. | |
| 8,911,442 B2 | 12/2014 | Wing et al. | |
| 8,940,007 B2 | 1/2015 | Smith et al. | |
| 9,186,192 B2 | 11/2015 | Biedermann et al. | |
| 9,693,762 B2 | 7/2017 | Reimels | |
| 9,844,400 B2 | 12/2017 | Stevenson et al. | |
| 9,907,583 B2 | 3/2018 | Hayes | |
| 10,792,168 B2 | 10/2020 | Malcolmson et al. | |
| 10,835,289 B2 | 11/2020 | Biester et al. | |
| 11,638,596 B2 * | 5/2023 | Biester | A61B 17/7037 |
| | | | 606/326 |
| 2003/0233098 A1 | 12/2003 | Markworth | |
| 2010/0152793 A1 | 6/2010 | Lowry et al. | |
| 2012/0016373 A1 * | 1/2012 | Impellizzeri | A61B 17/8897 |
| | | | 606/104 |
| 2012/0226283 A1 | 9/2012 | Meridew et al. | |
| 2014/0249532 A1 * | 9/2014 | Biedermann | A61B 17/88 |
| | | | 606/80 |
| 2015/0342620 A1 | 12/2015 | Winslow | |
| 2018/0014863 A1 | 1/2018 | Biester et al. | |
| 2020/0121365 A1 | 4/2020 | Biester et al. | |
| 2021/0038264 A1 | 2/2021 | Biester et al. | |

OTHER PUBLICATIONS

International Preliminary Report on Patentability for Application No. PCT/IB2019/058875, issued Apr. 14, 2021.

* cited by examiner

REAMER INSTRUMENTS AND RELATED METHODS

CROSS-REFERENCE TO RELATED APPLICATIONS

This application is a continuation of U.S. application Ser. No. 17/069,626, filed on Oct. 13, 2020. U.S. application Ser. No. 17/069,626 is a continuation of U.S. application Ser. No. 16/164,532, filed on Oct. 18, 2018, now issued as U.S. Pat. No. 10,835,289. The entire contents of each of these applications are incorporated by reference herein.

FIELD

Reamer instruments and related methods are disclosed herein, e.g., for reaming bone to facilitate in situ assembly of a bone anchor.

BACKGROUND

Bone anchors can be used in orthopedic surgery to fix bone during healing, fusion, or other processes. In spinal surgery, for example, bone anchors can be used to secure a rod or other spinal fixation element to one or more vertebrae to rigidly or dynamically stabilize the spine.

Bone anchors can be preassembled prior to use or can be at least partially assembled in situ. For example, bone anchors have been proposed in which a threaded shank portion of the bone anchor is initially driven into bone without an attached receiver head. At some later point in time, a receiver head can be attached to the implanted shank. The receiver head can be used to secure a rod or other stabilization element to the bone anchor. In some cases, the surrounding bone can interfere with assembly of the receiver head onto the shank. In these instances, a reamer or other instrument can be used to remove potentially interfering bone and create clearance for assembly of the bone anchor.

Existing reamers do not provide any indication to the user as to the degree of bone removal. This can lead to (1) inadvertent removal of too much bone, (2) removal of too little bone which, if not detected by the user, could result in compromised bone anchor assembly, and/or (3) repeated insertion and removal of the reamer to determine whether sufficient bone removal has occurred, undesirably complicating and lengthening the procedure.

A need exists for improved reamer instruments and related methods.

SUMMARY

Reamer instruments and related methods are disclosed herein, e.g., for reaming bone to facilitate in situ assembly of a bone anchor. In some embodiments, the instrument can include a feedback mechanism configured to alert the user when sufficient bone has been removed to facilitate assembly of the bone anchor. The feedback mechanism can be triggered by a movable shaft of the instrument that is displaced by the shank portion of the bone anchor as the surrounding bone is reamed.

In one aspect, a surgical instrument is provided that can include an outer shaft having a cutting element at a distal end thereof and an inner shaft slidably disposed within the outer shaft. The inner shaft can be configured to move longitudinally relative to the outer shaft as the cutting element is used to remove bone from around an implanted bone anchor shank. The instrument can further include a feedback mechanism configured to generate user feedback when the inner shaft moves longitudinally relative to the outer shaft by a threshold distance.

The instruments and methods described herein can include any of a variety of additional or alternative features, all of which are considered within the scope of the present disclosure. For example, in some embodiments the threshold distance can correspond with an amount of clearance space needed to assemble a receiver member to an implanted bone anchor shank. By way of further example, in certain embodiments the feedback mechanism can be configured to prevent relative longitudinal movement between the inner and outer shafts when the feedback mechanism is triggered.

In some embodiments, the feedback mechanism can include an indicator configured to move into a relief to generate at least one of audible, visual, and tactile feedback when the inner shaft is moved longitudinally relative to the outer shaft by the threshold distance. Moreover, in some embodiments the indicator can be movably coupled to the outer shaft and the relief can be formed in the inner shaft. In certain embodiments, the indicator can be movably coupled to the inner shaft and the relief can be formed in the outer shaft. In some embodiments, the indicator can have an opening through which the inner shaft passes, and the opening can have a central axis. Further, in some embodiments the indicator can be movable between a first position in which the central axis of the indicator opening is aligned with a central axis of the inner shaft such that relative longitudinal movement of the inner and outer shafts is not limited by the indicator, and a second position in which the central axis of the indicator opening is offset from the central axis of the inner shaft and a portion of the indicator is received within the relief of the inner shaft, such that the indicator interferes with relative longitudinal movement of the inner and outer shafts.

In certain embodiments, the feedback mechanism can include an indicator configured to move longitudinally relative to the outer shaft as the inner shaft moves longitudinally relative to the outer shaft, and the indicator can be visible through an opening formed in a proximal end cap of the instrument. In some embodiments, the indicator can be flush with, protrude from, or be recessed with respect to an outer surface of the instrument when the inner shaft moves longitudinally relative to the outer shaft by the threshold distance.

In some embodiments, the distal end of the inner shaft can have a bearing surface configured to contact and slide across a head portion of an implanted bone anchor shank as the instrument is used to remove bone from around the implanted bone anchor shank.

In certain embodiments, the instrument can further include a collection chamber in fluid communication with at least one of (a) a cannulation formed in the inner shaft and (b) a space defined between the inner and outer shafts, such that material removed by the instrument is collected in the chamber.

In some embodiments, the cutting element can include a plurality of longitudinally-extending flutes spaced about an outer perimeter of the outer shaft. In certain embodiments, the flutes can be at least one of (a) helical, (b) bi-directional, (c) interrupted along their length by one or more radial grooves, (d) have a non-zero rake angle, and (e) have distal-facing surfaces that are angled radially inwards.

In certain embodiments, the feedback mechanism can include one or more markings of the inner shaft visible through a window formed in the outer shaft and one or more markings of the outer shaft, the markings of the inner and outer shafts providing a visual indication as to the degree of longitudinal movement of the inner shaft relative to the outer shaft.

In some embodiments, the instrument can further include a driver shaft inserted through the inner shaft and configured to apply torque to a bone anchor shank. Further, in some embodiments the inner shaft can include a plurality of flexible and resilient fingers configured to grasp a head portion of a bone anchor shank.

In another aspect, a surgical method is provided that can include driving a shank of a bone anchor into bone, positioning a reamer instrument over the implanted shank, and manipulating the reamer instrument relative to the shank to remove bone from around the shank. Further, the reamer instrument can have an inner shaft slidably mounted within an outer shaft. The method can further include, as bone is removed by the reamer instrument, advancing the outer shaft distally relative to the bone while the shank axially displaces the inner shaft in a proximal direction relative to the outer shaft, as well as generating feedback indicative of a degree of bone removal using a feedback mechanism of the reamer instrument. Moreover, the feedback mechanism can be configured to trigger when the inner shaft moves relative to the outer shaft by a threshold distance.

As with the aspects and embodiments described above, a number of additional or alternative features can be included that are considered within the scope of the present disclosure. For example, in some embodiments driving the shank can include rotating the shank relative to the bone using a driver shaft inserted through the inner shaft of the reamer instrument.

In other embodiments, positioning the reamer instrument can include inserting a head portion of the shank into an open distal end of the outer shaft of the instrument and contacting the head portion with the inner shaft of the instrument.

In certain embodiments, manipulating the reamer instrument can include at least one of (a) rotating the outer shaft of the instrument relative to a head portion of the shank about a central longitudinal axis of the outer shaft and (b) polyaxially articulating the outer shaft of the instrument relative to the head portion of the shank.

In some embodiments, generating feedback can include axially moving an indicator as the inner shaft is displaced axially, the indicator being flush with, protruding from, or recessed with respect to an outer surface of the instrument when the inner shaft moves relative to the outer shaft by the threshold distance.

In certain embodiments, the threshold distance can correspond with an amount of bone removal sufficient to assemble a receiver member to the implanted shank.

In some embodiments, the method can further include separating the instrument from the shank and attaching a receiver member to the implanted shank. And in some embodiments, the method can further include retaining the shank to the instrument by grasping the head of the shank between a plurality of fingers of the inner shaft.

Any of the features or variations described above can be applied to any particular aspect or embodiment of the present disclosure in a number of different combinations. The absence of explicit recitation of any particular combination is due solely to the avoidance of repetition in this summary.

DETAILED DESCRIPTION

Reamer instruments and related methods are disclosed herein, e.g., for reaming bone to facilitate in situ assembly of a bone anchor. In some embodiments, the instrument can include a feedback mechanism configured to alert the user when sufficient bone has been removed to facilitate assembly of the bone anchor. The feedback mechanism can be triggered by a movable shaft of the instrument that is displaced by the shank portion of the bone anchor as the surrounding bone is reamed. A clearance test instrument and related methods are also disclosed herein without cutting or reaming elements, e.g., for testing or checking whether there is sufficient clearance surrounding the head of the screw shank to allow for proper head assembly.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Figure 1A:
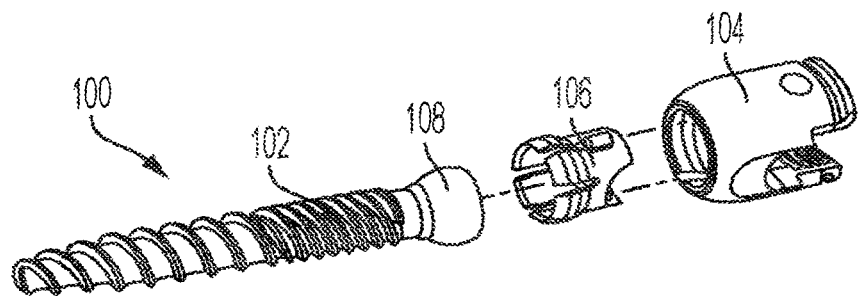
FIG. 1A is an exploded perspective view of a bone anchor.

FIG. 1A illustrates an exemplary bone anchor 100 with which one or more of the instruments described herein can be used. It will be appreciated that the illustrated bone anchor 100 is exemplary and that the instruments described herein can be used with any of a variety of bone anchors. The illustrated bone anchor 100 includes an anchor portion or shank 102, a head or receiver member 104 for receiving a spinal fixation element, such as a spinal rod, to be coupled to the shank 102, and a collet or retention member 106 for maintaining the head and the shank in an assembled state. Additional details of the bone anchor 100 and other exemplary bone anchors that can be used with the instruments described herein can be found in U.S. Publication No. 2018/0014863 filed on Jun. 15, 2017 and entitled "BONE ANCHOR ASSEMBLIES AND RELATED INSTRUMENTATION," which is hereby incorporated by reference herein.

Figure 1B:
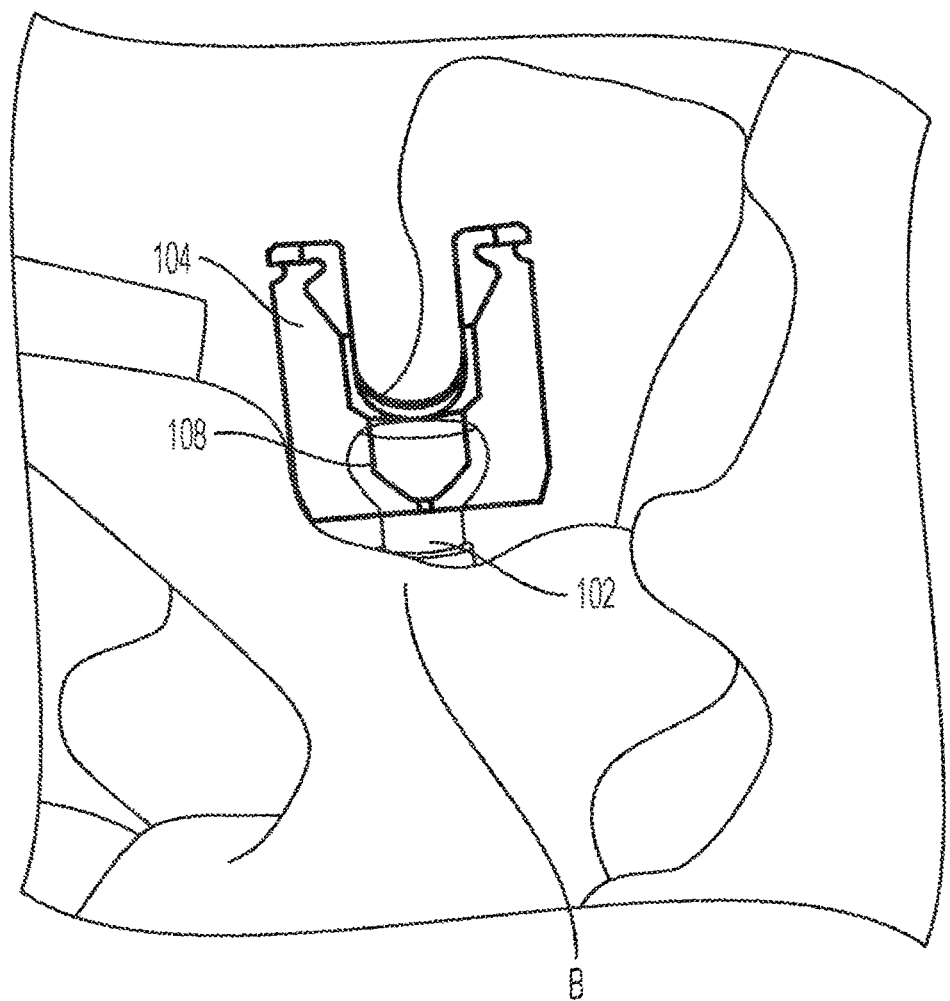
FIG. 1B is a perspective view of a bone anchor shank implanted in bone with sufficient clearance for attachment of a receiver head (shown in phantom)
Figure 1C:
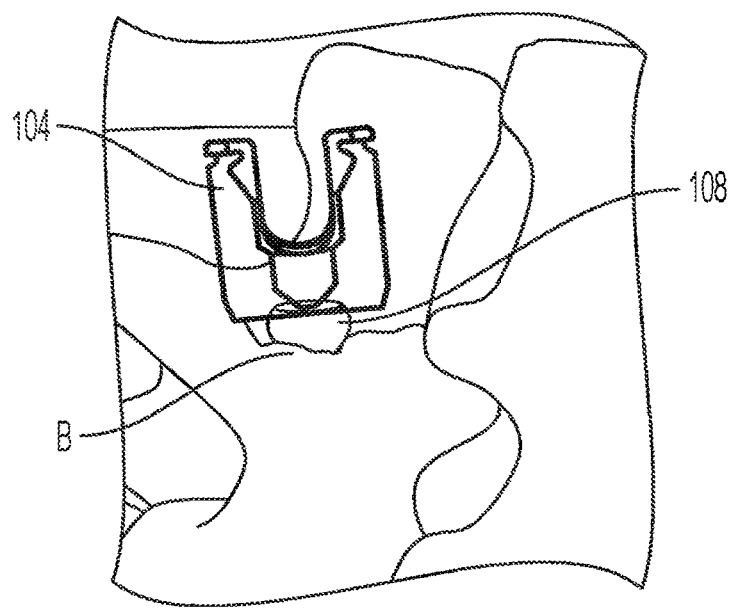
FIG. 1C is a perspective view of a bone anchor shank implanted in bone with insufficient clearance for attachment of a receiver head (shown in phantom)
Figure 1D:
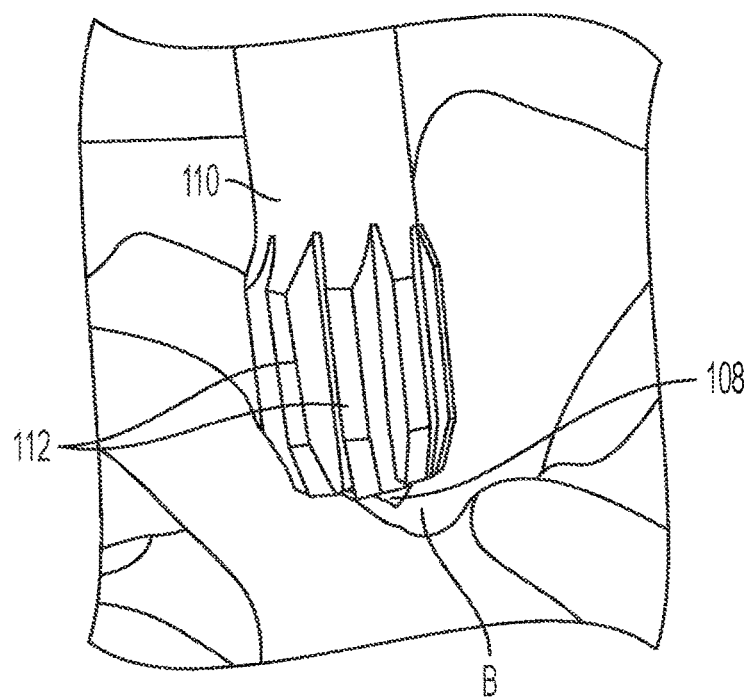
FIG. 1D is a perspective view of a reamer instrument in use to remove bone from around a bone anchor shank.
Figure 1E:
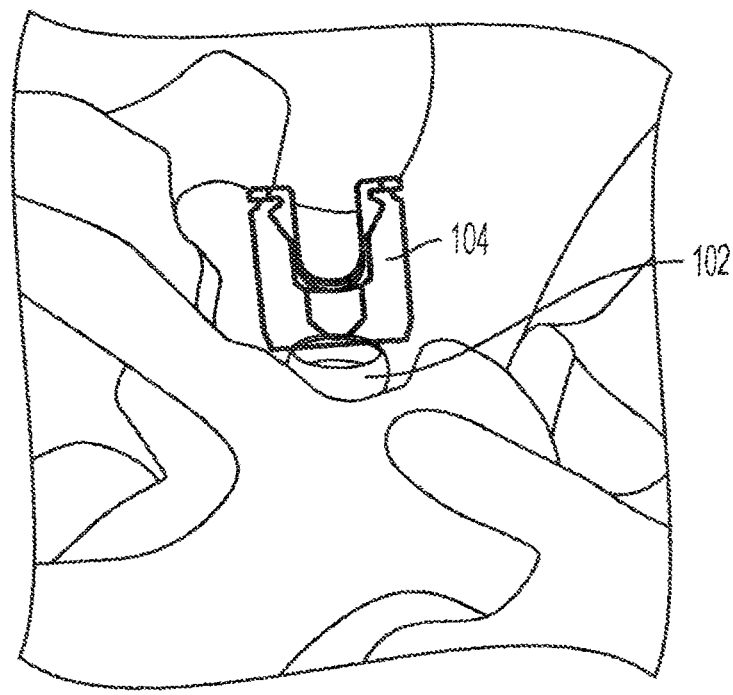
FIG. 1E is a perspective view of a bone anchor shank implanted in bone with insufficient reaming for attachment of a receiver head (shown in phantom)
Figure 1F:
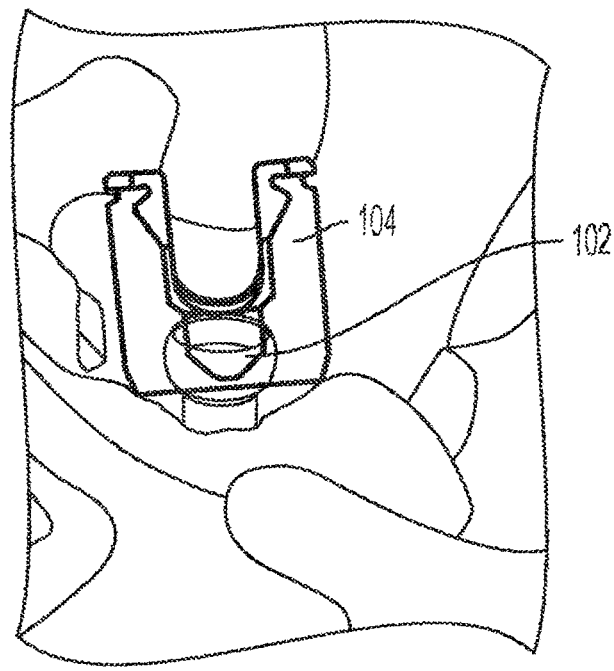
FIG. 1F is a perspective view of a bone anchor shank implanted in bone with sufficient clearance for attachment of a receiver head (shown in phantom)

The bone anchor 100 can be configured for in situ assembly. For example, the shank portion 102 of the bone anchor 100 can be initially driven into bone without the receiver member 104 being attached thereto. At some later point in time, the receiver member 104 can be attached to the implanted shank 102. The receiver member 104 can be used to secure a rod or other stabilization element to the bone anchor 100. The receiver member 104 can be assembled to the shank 102 by inserting the head 108 of the shank proximally into an open distal end of the receiver member, e.g., by advancing the receiver member distally over the implanted shank. As shown in FIG. 1B, in order for the receiver member 104 to be advanced far enough in the distal direction to complete the assembly, there must be adequate clearance with the surrounding bone B. As shown in FIG. 1C, if the shank head 108 is buried too low, inadequate clearance with the surrounding bone B can prevent assembly of the receiver member 104 thereto. In this instance, as shown in FIG. 1D, a reamer instrument 110 of the type described herein can be positioned over the head 108 of the shank 102 and moved relative to shank to remove potentially interfering bone B. For example, the reamer instrument 110 can be rotated about its central longitudinal axis and/or articulated polyaxially relative to the shank head 108 to clear away the bone B using cutting flutes 112 formed at the distal end of the reamer instrument. If inadequate reaming occurs, as shown in FIG. 1E, insufficient clearance with surrounding bone makes it difficult or impossible to assemble the receiver member 104 to the shank 102. When adequate reaming is performed, as shown in FIG. 1F, sufficient clearance exists with the surrounding bone to allow the receiver member 104 to be assembled to the shank 102. As described further below, the reamer instruments disclosed herein can be configured to provide feedback or indication to the user when the degree of bone removal is sufficient to allow assembly, e.g., when bone has been removed to the degree shown in FIG. 1F.

FIGS. 2A-2I illustrate an exemplary embodiment of a reamer instrument 200 that can be used, for example, for reaming bone to facilitate in situ assembly of a bone anchor. As shown, the instrument 200 can include an outer shaft 202, an inner shaft 204, and a feedback mechanism 206, e.g., in the form of a spring-loaded indicator 208. The outer shaft 202 can include flutes or other cutting features 210 configured to remove bone when the outer shaft is manipulated relative to the bone. The inner shaft 204 can be slidably mounted within the outer shaft 202 and can be configured to trigger the feedback mechanism 206 when sufficient bone removal has occurred. In particular, as the outer shaft 202 is manipulated to remove bone surrounding an implanted bone anchor shank, the shank can displace the inner shaft 204 proximally relative to the outer shaft. The degree of displacement of the inner shaft 204 can correspond with the degree of bone removal. When displaced beyond a predetermined threshold distance, a relief 212 formed in the inner shaft 204 can be aligned with the indicator 208, allowing movement of the indicator to provide tactile, audible, and/or visual feedback to a user. In some embodiments, for example, the indicator 208 can be a button configured for a user to contact to receive tactile feedback. In other embodiments, however, the indicator 208 need not be contacted to convey feedback, e.g., its position can visually convey feedback, etc.

The outer shaft 202 can include an elongate, generally-cylindrical body having a proximal end 202p and a distal end 202d and extending along a central longitudinal axis A1. The outer shaft 202 can define a central passage 214 extending between the proximal and distal ends 202p, 202d. The inner shaft 204 can be coaxially received within the central passage 214, such that the central axis A1 of the outer shaft 202 is collinear with the central axis A2 of the inner shaft 204.

The distal end 202d of the outer shaft 202 can include flutes 210 for removing bone. While a plurality of longitudinally extending flutes 210 are shown, it will be appreciated that any of a variety of bone removal features, in any number, can be used instead or in addition, including blades, teeth, roughened surfaces, and the like. Various flute arrangements and configurations that can be used with the instrument 200 are described further below. The flutes or other cutting features 210 can be treated with a coating, including hard coatings such as titanium nitride, to increase the durability and usable life of the instrument 200. The number of flutes 210 can vary, e.g., depending on the diameter of the instrument 200 or the diameter of hole to be reamed.

The outer shaft 202 can include features to facilitate grasping and manipulating the outer shaft. For example the outer shaft 202 can include a proximal handle 216. The handle 216 can be formed integrally with the outer shaft 202 or, as shown, can be a separate component mated to the outer shaft. The handle 216 can define a lumen in which at least a portion of the outer shaft 202 is received, and can be secured thereto using a cross-pin or other attachment feature. An outer surface of the handle 216 can be textured, faceted, knurled, grooved, etc. to facilitate gripping of the handle. The handle 216 can include a ratcheting mechanism, which can improve efficiency and reduce user fatigue. The outer shaft 202 can include a modular coupling to facilitate attachment of any of a variety of handle types or sizes thereto. Exemplary handle types can include T-shaped handles, pencil grip handles, pistol grip handles, knob-shaped handles, and so forth.

The outer shaft 202 can define a cavity 218 for housing the feedback mechanism 206. The cavity 218 can be formed in an enlarged diameter proximal portion of the outer shaft 202 as shown. The cavity 218 can be open to a sidewall of the outer shaft 202 and can intersect with the central passage 214. The cavity 218 can be sized and shaped to substantially correspond to the size and shape of an indicator 208 of the feedback mechanism 206. The indicator 208 can be slidably received within the cavity 218 such that the indicator can move within the cavity towards and away from the central passage 214, e.g., in a direction perpendicular to the axis A1. The floor of the cavity 218 can include a first bore 220 in which at least a portion of an indicator spring 222 of the feedback mechanism 206 can be received. The outer shaft 202 can include an opening 224 formed in a sidewall of the outer shaft that intersects with the cavity 218. The opening 224 can extend perpendicular to the axis A1 as shown. The opening 224 can be configured to receive at least a portion of a retention pin 226 of the feedback mechanism 206 therein.

As described further below, the outer shaft 202 can receive a retention element 228 for maintaining the inner shaft 204 within the central passage 214 of the outer shaft. For example, a proximal portion of the central passage 214 can have an enlarged diameter, defining a stop shoulder 238 at the transition between the proximal portion and the distal portion. The proximal portion of the central passage 214 can be threaded or otherwise configured for mating with a retention element 228.

The inner shaft 204 can include an elongate, generally-cylindrical body having a proximal end 204p and a distal end 204d and extending along a central longitudinal axis A2. The body of the shaft 204 can be solid or can be cannulated, e.g., to allow passage of a guidewire therethrough or to allow vacuum suction to be applied therethrough.

The distal end 204d of the inner shaft 204 can include a bearing surface 230 configured to contact and bear against the head of a shank implanted in bone as the instrument 200 is used to remove bone from around the shank. The bearing surface 230 can have a geometry that is complementary to that of a bone anchor shank with which the instrument 200 is to be used. For example, the bearing surface 230 can form a negative of the outer surface of the head of the shank. As another example, the bearing surface 230 can have a concave spherical shape. The bearing surface 230 can be configured to slide across the proximal surface of the shank, e.g., as the instrument 200 is rotated axially relative to the shank and/or as the instrument is polyaxially articulated relative to the shank.

The inner shaft 204 can include one or more reliefs 212 for receiving at least a portion of the indicator 208 when a predetermined threshold axial displacement of the inner shaft relative to the outer shaft 202 is reached. The relief 212 can be defined by a groove or slot formed in an outer surface of the inner shaft 204. The position of the relief 212 along the length of the inner shaft 204 can be selected to define the displacement threshold at which the feedback mechanism 206 is triggered. Moving the relief 212 closer to the distal end 204d of the inner shaft 204 can cause the feedback mechanism 206 to trigger later, resulting in more bone removal before triggering. Moving the relief 212 closer to the proximal end 204p of the inner shaft 204 can cause the feedback mechanism 206 to trigger earlier, resulting in less bone removal before triggering. It will be appreciated that the position of the relief 212 along the inner shaft 204 can be calibrated to the clearance space needed to assemble a bone anchor with which the instrument 200 is to be used.

The proximal end 204p of the inner shaft 204 can receive a retention element 232 for maintaining the inner shaft within the central passage 214 of the outer shaft 202. For example, the proximal end 204p of the inner shaft 204 can include an exterior thread onto which a retention nut 232 can be threaded.

The instrument 200 can include a bias element 234 configured to bias the inner shaft 204 distally relative to the outer shaft 202. For example, the instrument 200 can include a coil spring 234 disposed coaxially over the inner shaft 204. One end of the spring 234 can bear against a washer 236 disposed in the central passage 214 of the outer shaft 202 and the opposite end of the spring can bear against an enlarged diameter portion of the inner shaft 204, such that the spring urges the inner shaft in a distal direction relative to the outer shaft. While a distally biased inner shaft 204 is shown, in other arrangements the inner shaft can be biased in a proximal direction.

The illustrated instrument includes a retention element in the form of a threaded plug 228 received within a proximal end of the outer shaft 202. It will be appreciated that any of a variety of other retention features can be used instead or in addition. As shown, the plug 228 can include a threaded exterior surface that mates with a threaded interior surface of the outer shaft 202 to retain the washer 236 and inner shaft 204 therein. The plug 228 can define a central passage in which a proximal portion of the inner shaft 204 is received. A nut 232 attached to the proximal end of the inner shaft 204 can interact with the washer 236 to define a distal travel limit. In particular, a distal-facing surface of the nut 232 can contact a proximal facing surface of the washer 236 to prevent further distal movement of the inner shaft 204 relative to the outer shaft 202.

The distal limit can be adjusted by changing the longitudinal position of the nut 232 along the inner shaft 204, e.g., by rotating the nut to cause it to travel along the thread of the inner shaft. This can allow use with multiple types of bone anchors, multiple types of modular receiver members or other bone anchor components, or in different situations that may be encountered during a surgery. For example, the nut 232 can be moved proximally along the inner shaft 204 to allow the inner shaft to move further in the distal direction relative to the outer shaft 202. This can allow the inner shaft 204 to engage with a shank that is buried deeper in surrounding bone at the time the reaming operation is started. Also, in the event of a manual override or malfunction of the indicator trigger 206, this can cause the nut 232 to contact the distal-facing surface of the retention plug 228 sooner to limit the maximum amount of reaming permitted.

Figure 2A:
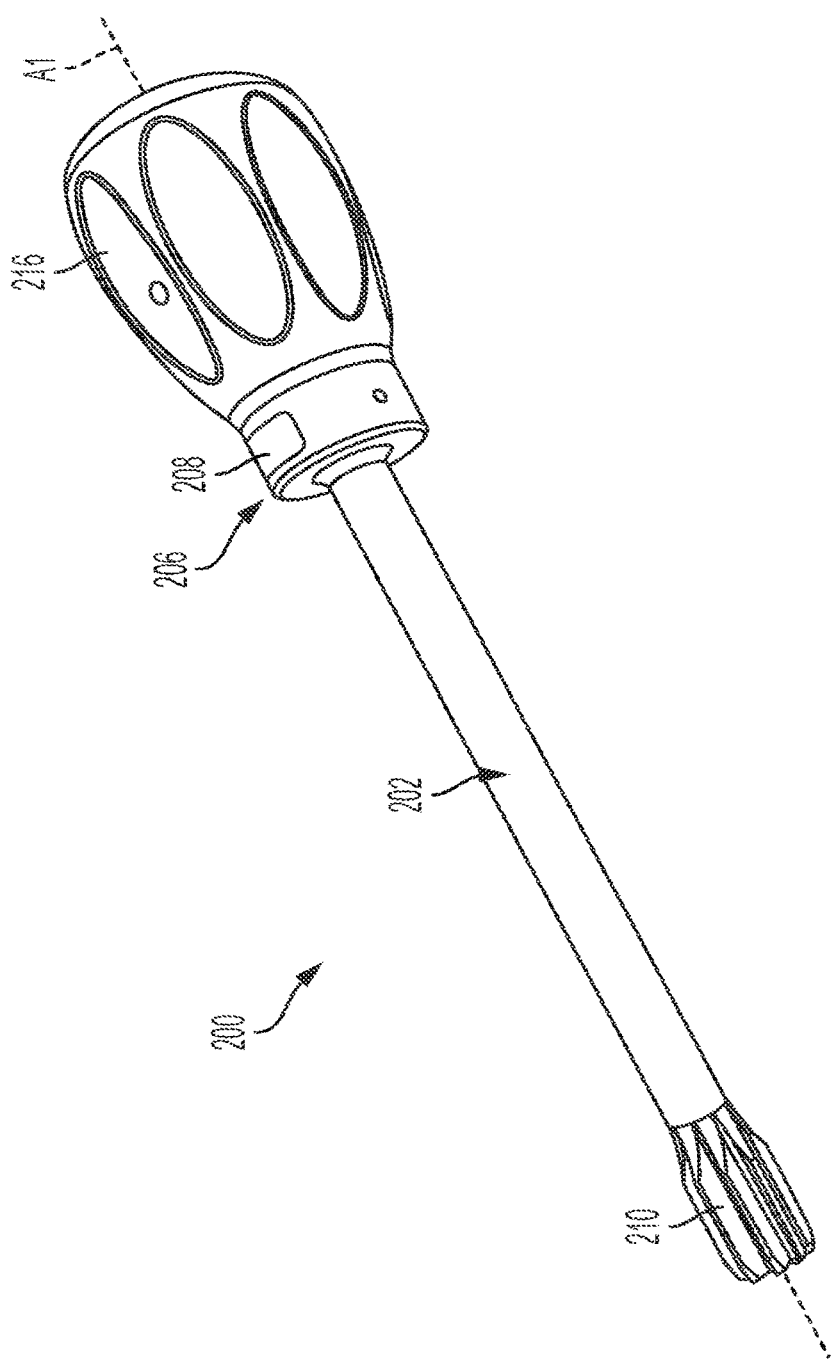
FIG. 2A is a perspective view of a reamer instrument.
Figure 2B:
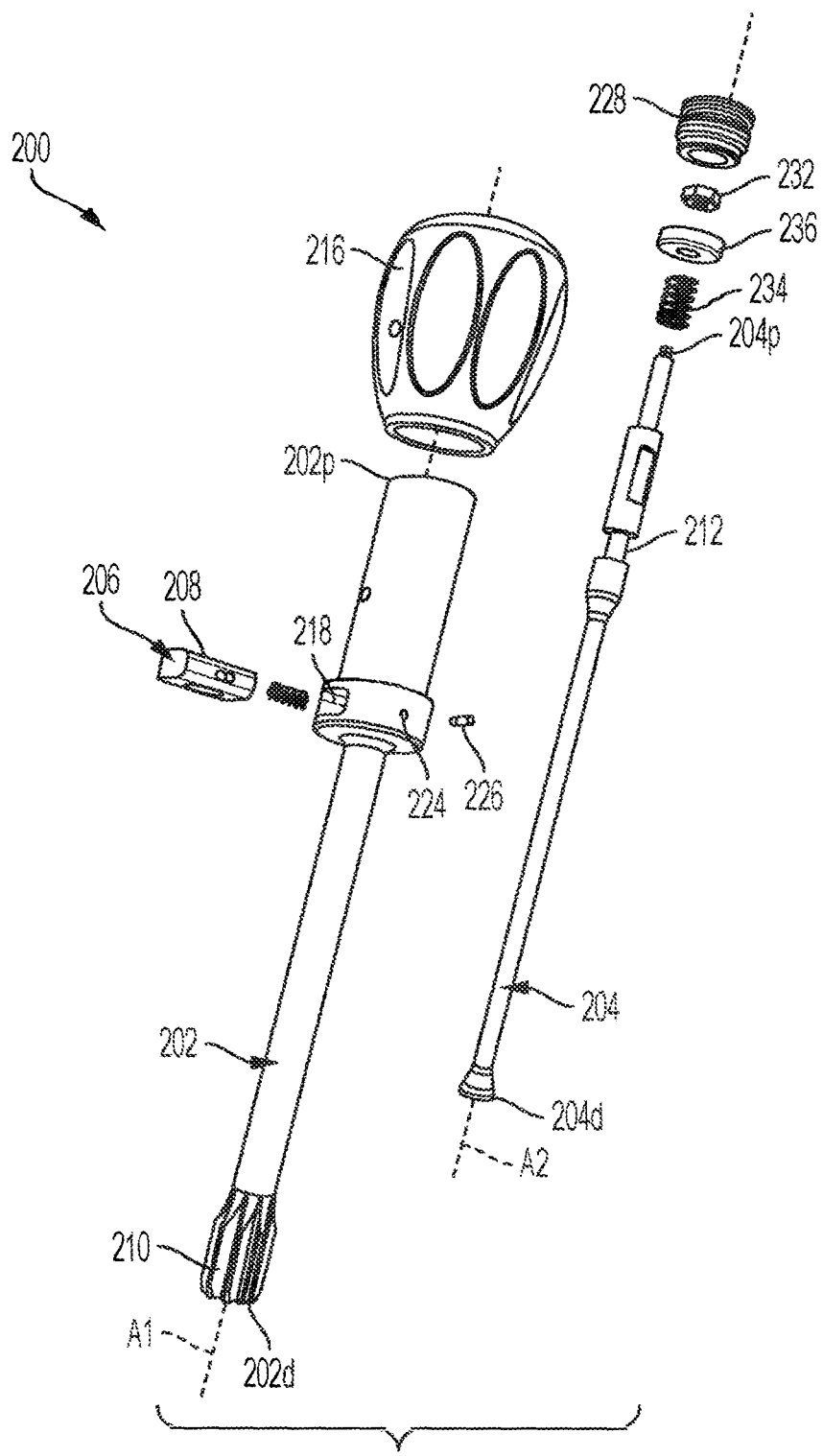
FIG. 2B is an exploded perspective view of the instrument of FIG. 2A.
Figure 2C:
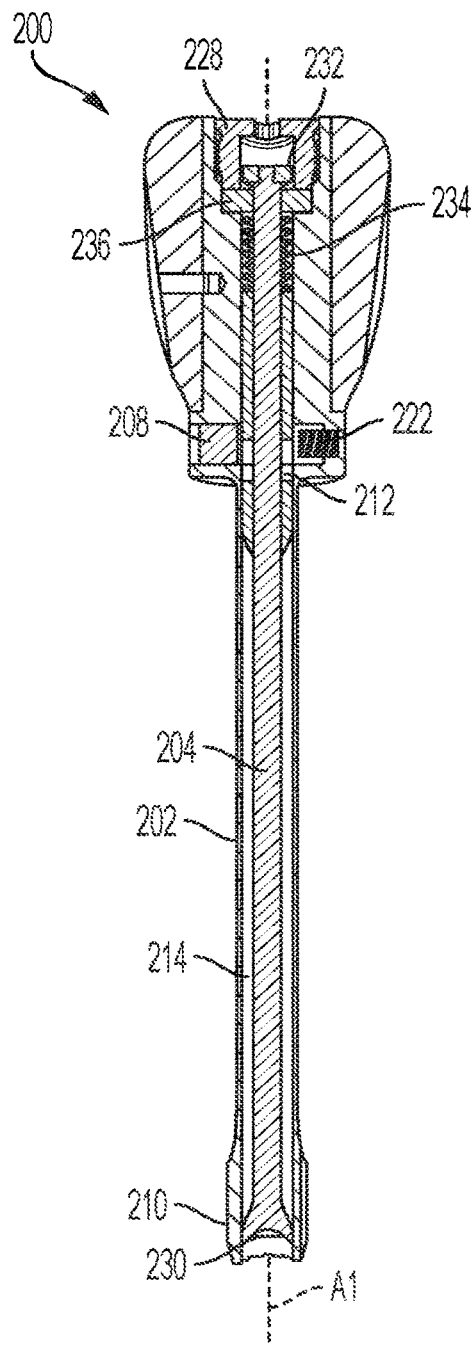
FIG. 2C is a sectional side view of the instrument of FIG. 2A in a first operating state.
Figure 2D:
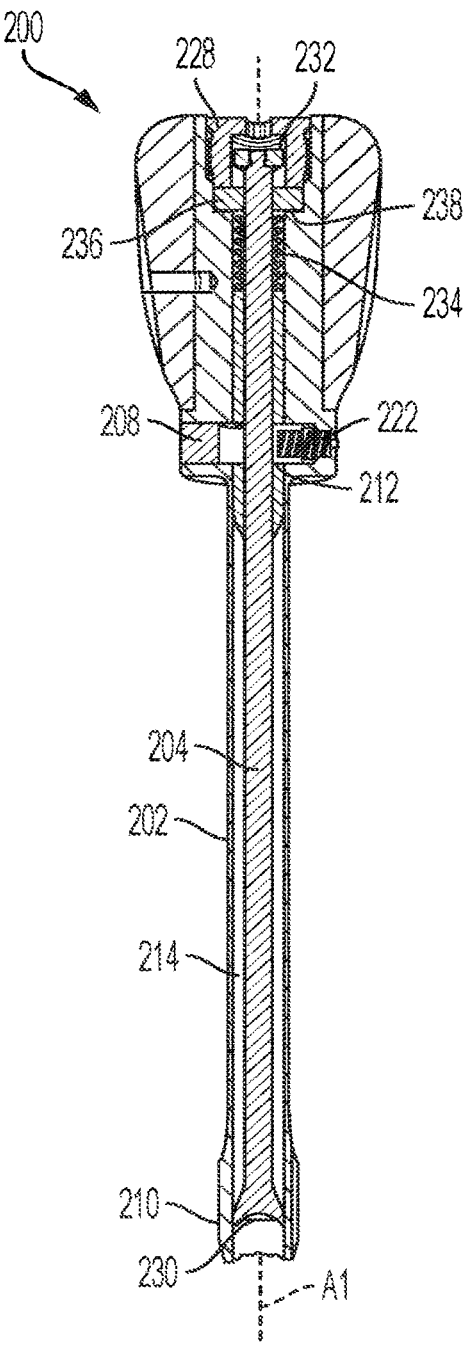
FIG. 2D is a sectional side view of the instrument of FIG. 2A in a second operating state.
Figure 2E:
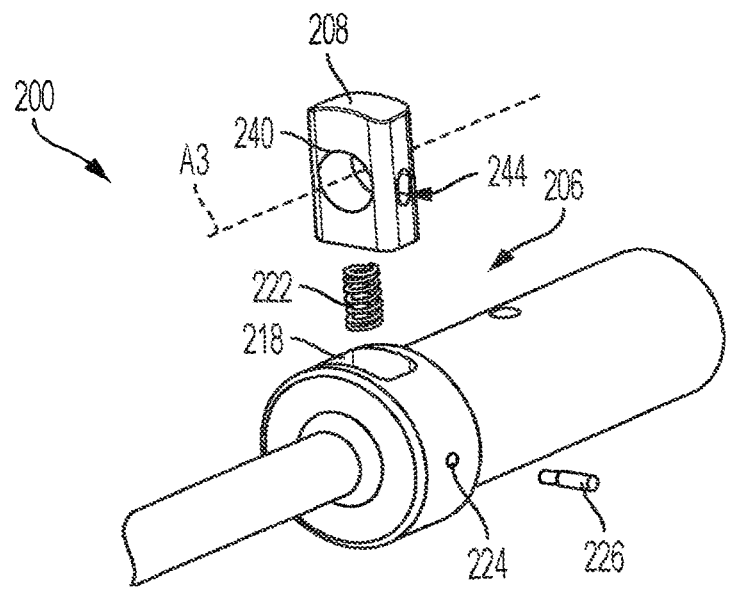
FIG. 2E is an exploded perspective detail view of a feedback mechanism of the instrument of FIG. 2A.
Figure 2F:
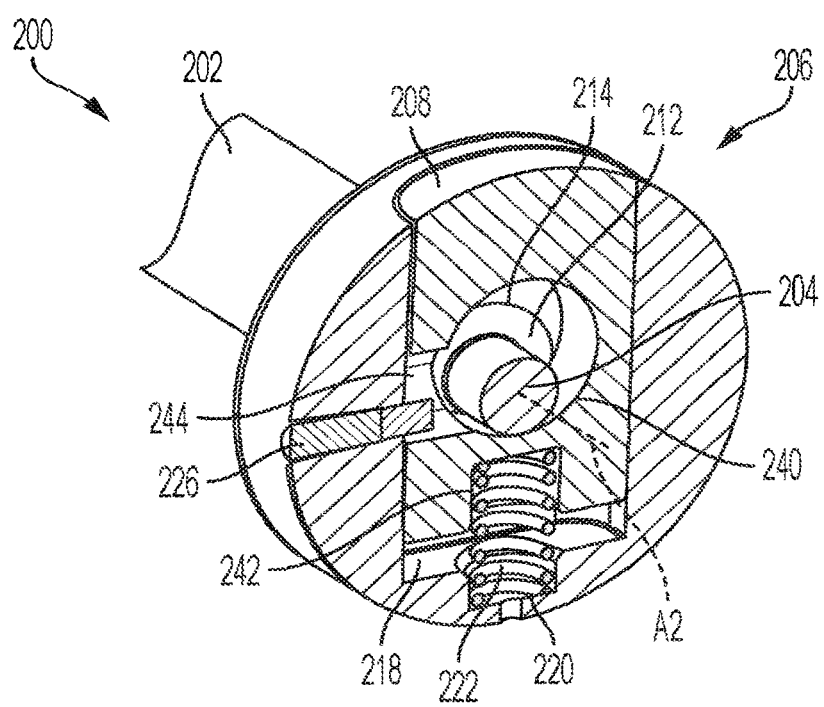
FIG. 2F is a sectional end view of the instrument of FIG. 2A.

The feedback mechanism 206 is shown in greater detail in FIGS. 2E-2F. As shown, the feedback mechanism 206 can include an indicator 208 with a corresponding indicator spring 222 and a retention pin 226. The indicator 208 can include a substantially rectangular-parallelepiped body having proximal and distal abutment surfaces. A cylindrical opening 240 can be formed through the indicator 208, extending between the proximal and distal surfaces. The opening 240 can include a central longitudinal axis A3. The opening 240 can have a diameter or dimension that is greater than a maximum outer diameter or dimension of the inner shaft 204. Accordingly, when the central longitudinal axis A2 of the inner shaft 204 is coaxial with the central longitudinal axis A3 of the opening 240, the indicator 208 does not interfere with longitudinal translation of the inner shaft relative to the indicator. As discussed further below, however, the indicator 208 can be positioned such that the axis A3 of the opening 240 is offset from the axis A2 of the inner shaft 204 and such that the indicator does interfere with longitudinal translation of the inner shaft relative thereto.

The indicator spring 222 can be partially received within the first bore 220 formed in the bottom of the cavity 218 and partially received within a second bore 242 formed in the sidewall of the indicator 208 that faces the bottom of the cavity. The indicator spring 222 can thus be effective to bias the indicator 208 away from the bottom of the cavity 218 such that the indicator is urged in a radially-outward direction. The retention pin 226 can extend through the opening 224 formed in the sidewall of the outer shaft 202 and into an elongated slot 244 formed in the indicator 208. The retention pin 226 can thus limit the travel of the indicator 208 within the cavity 218 to prevent the indicator from falling out of the instrument 200. The retention pin 226 can be welded or otherwise secured to the outer shaft 202 after assembly to prevent inadvertent disassembly.

The indicator 208 can be slidable within the cavity 218 between at least a first, released position and a second, engaged position. The indicator 208 can be biased towards the engaged position and can be configured to move from the engaged position to the released position when depressed by a user.

In the released or disengaged position, the axis A3 of the indicator opening 240 is aligned with the axis A2 of the inner shaft 204 such that longitudinal translation of the inner shaft is not limited by the indicator 208. Rather, the indicator 208 is moved out of the path of the inner shaft 204, such that the indicator does not restrict longitudinal movement of the inner shaft relative to the outer shaft 202. In this position, the inner shaft 204 is free to translate distally until the nut 232 contacts the washer 236, and is free to translate proximally until the relief 212 of the inner shaft is aligned with the indicator 208. The inner shaft 204 can have an outer diameter sufficient to maintain the indicator 208 in the disengaged position when the relief 212 of the inner shaft is not aligned with the indicator. The indicator 208 can also be maintained in the disengaged position by manual user pressure applied to the indicator, e.g., when it is desired to ream bone beyond the threshold setting of the instrument 200 or to allow disassembly of the instrument.

In the engaged position, the bias of the indicator spring 222 urges the indicator 208 upwards such that a portion of the indicator is received within the relief 212 of the inner shaft 204, preventing further proximal movement of the inner shaft relative to the outer shaft 202.

While a single indicator 208 is shown, it will be appreciated that the instrument 200 can include any number of indicators, e.g., two or more. The indicator can be axially actuated instead of or in addition to being radially actuated as in the illustrated embodiment.

Operation of the instrument 200 is illustrated schematically in FIGS. 2C-2D.

In FIG. 2C, the instrument 200 is shown in a first operating state in which the instrument is prepared to begin reaming bone. The inner shaft 204 is advanced distally relative to the outer shaft 202 under the bias of the spring 234 until the nut 232 contacts the washer 236 to prevent further distal travel. The relief 212 of the inner shaft 204 is longitudinally-offset from the indicator 208, such that the outer sidewall of the inner shaft maintains the indicator in the disengaged position. Accordingly, the indicator 208 does not restrict proximal translation of the inner shaft 204 relative to the outer shaft 202 and the indicator is recessed relative to the outer surface of the outer shaft.

As the instrument 200 is used to ream bone from around a shank of a bone anchor, the outer shaft 202 travels distally into the void created where the removed bone was previously situated and the shank moves proximally into the outer shaft, axially displacing the inner shaft 204 in a proximal direction.

In FIG. 2D, the instrument 200 is shown in a second operating state in which sufficient bone has been removed to trigger the feedback mechanism 206 of the instrument. The inner shaft 204 is displaced proximally relative to the outer shaft 202 until the relief 212 is aligned with the indicator 208. When so-aligned, the sidewall of the inner shaft 204 no longer maintains the indicator 208 in the disengaged position and the indicator is free to travel into the relief 212 under the bias of the indicator spring 222. In this engaged position, interference between the abutment surfaces of the indicator 208 and the sidewalls of the relief 212 prevent further proximal movement of the inner shaft 204 relative to the outer shaft 202, thereby limiting the depth of bone removal. Movement of the indicator 208 can generate tactile and/or audible feedback to the user, indicating that the threshold amount of reaming has been completed. The user can also observe that the indicator 208 is now flush with, protruding from, or recessed to a lesser degree with respect to, the outer surface of the outer shaft 202, providing visual feedback that the threshold has been reached.

To return the instrument 200 to the first operating state, the user can separate the instrument from the bone anchor and manually push the indicator 208, allowing the inner shaft 204 to spring distally relative to the outer shaft 202 under the bias of the spring 234.

In use, the shank of a bone anchor can be driven into a bone. The reamer instrument 200 can then be positioned over the implanted bone anchor shank to remove surrounding bone in preparation for assembly of a receiver member to the shank. In particular, the head of the shank can be inserted into the open distal end of the outer shaft 202. The instrument 200 can be manipulated relative to the shank to remove bone from around the shank. For example, the outer shaft 202 can be rotated relative to the shank about the axis A1 and/or can be polyaxially articulated relative to the shank head. As bone is removed by the cutting flutes 210, the outer shaft 202 can move distally relative to the bone while the shank axially displaces the inner shaft 204 in a proximal direction relative to the outer shaft. When the degree of proximal displacement is sufficient to align the relief 212 with the indicator 208, the indicator 208 can spring, snap, or click into the engaged position, thereby providing tactile, audible, and/or visual feedback to the user that a threshold amount of bone has been removed. The threshold amount can be an amount sufficient to ensure there is enough clearance to assemble a receiver member to the implanted shank. The instrument 200 can be separated from the shank and removed from the patient, and a receiver member can be attached to the shank using known techniques. The assembled bone anchor can be used to secure a rod or other fixation element to the bone of the patient.

Figure 2G:
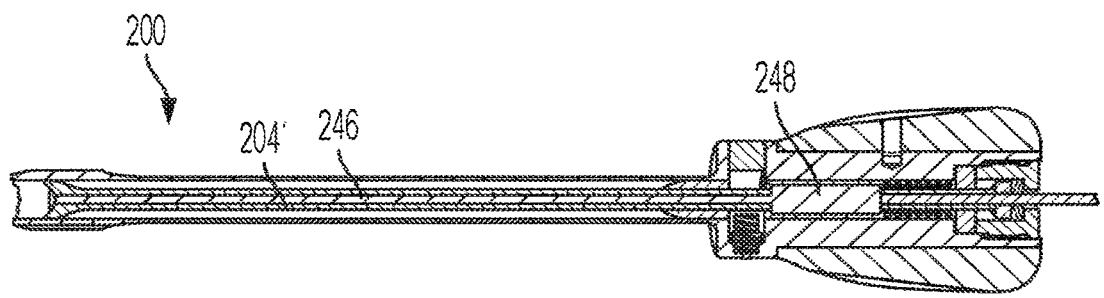
FIG. 2G is a sectional side view of the instrument of FIG. 2A, shown with an inner shaft having a collection chamber.
Figure 2H:
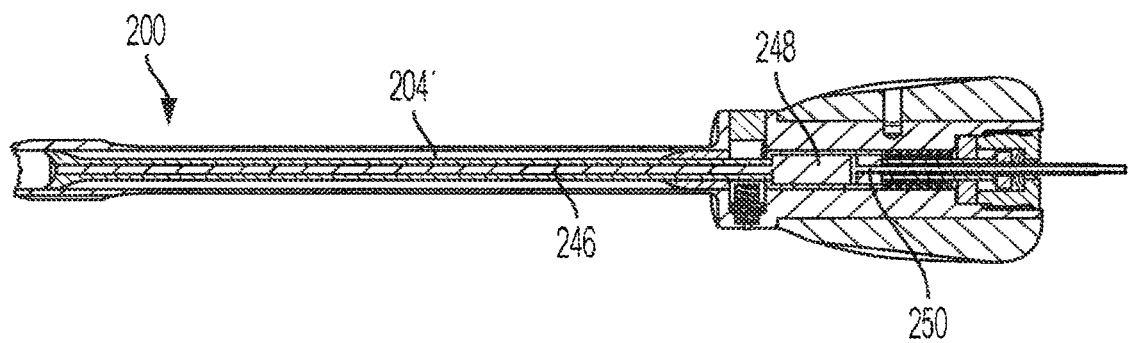
FIG. 2H is a sectional side view of the instrument of FIG. 2A, shown with an inner shaft having a collection chamber and a plunger for dispensing material from the collection chamber.
Figure 2I:
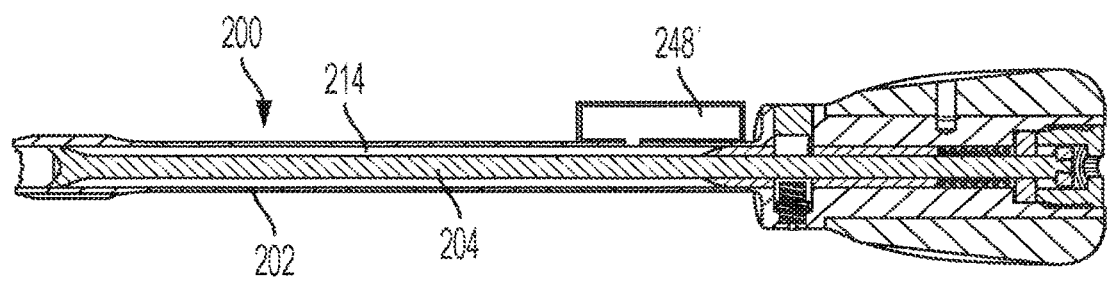
FIG. 2I is a sectional side view of the instrument of FIG. 2A, shown with an outer shaft having a collection chamber.

The instrument 200 can include tissue or bone collection features. As shown in FIG. 2G, for example, the inner shaft 204' can include a cannulation 246 to allow bone or other material cut by the instrument 200 to pass through the inner shaft. The material can be pulled through the inner shaft 204' by suction applied by a vacuum source coupled to the proximal end of the shaft. The material can be moved through the inner shaft 204' by an Archimedes screw or helical inner thread of the shaft. The material can be moved through the inner shaft 204' by displacement as additional material enters the distal end of the shaft. Material can be captured within a collection chamber 248 formed in the instrument 200, e.g., within the inner shaft 204' as shown. Alternatively, or in addition, material can be withdrawn through an opening at the proximal end of the instrument 200 and collected in an external chamber. Collected material can be harvested for subsequent use as graft material. As shown in FIG. 2H, the instrument 200 can include a plunger 250 for dispending collected material. In use, the plunger 250 can be urged distally to expel collected material from a distal end of the instrument 200. As shown in FIG. 2I, material can be collected via the clearance space 214 defined between the inner shaft 204 and the outer shaft 202. Material can be moved along the clearance space 214 by suction, an Archimedes screw or helical thread, displacement, or the like. The material can be collected in the void space 214 and/or can be collected in an external collection chamber 248'. The collection chamber 248' can be mounted to a sidewall of the instrument 200. The flutes or other cutting features 210 of the instrument 200 can be configured to encourage movement of cut or severed material towards the collection path of the instrument. For example, the distal-facing surfaces of the flutes 210 can be angled radially inwards to direct bone towards an inner cannulation of the instrument 200.

The instrument 200 can be configured to receive a driver shaft therethrough. For example, the instrument 200 can include a driver shaft inserted through a central cannulation of the inner shaft 204. The driver shaft can be used, before or after reaming, to drive the shank of a bone anchor into the bone.

Figure 3A:
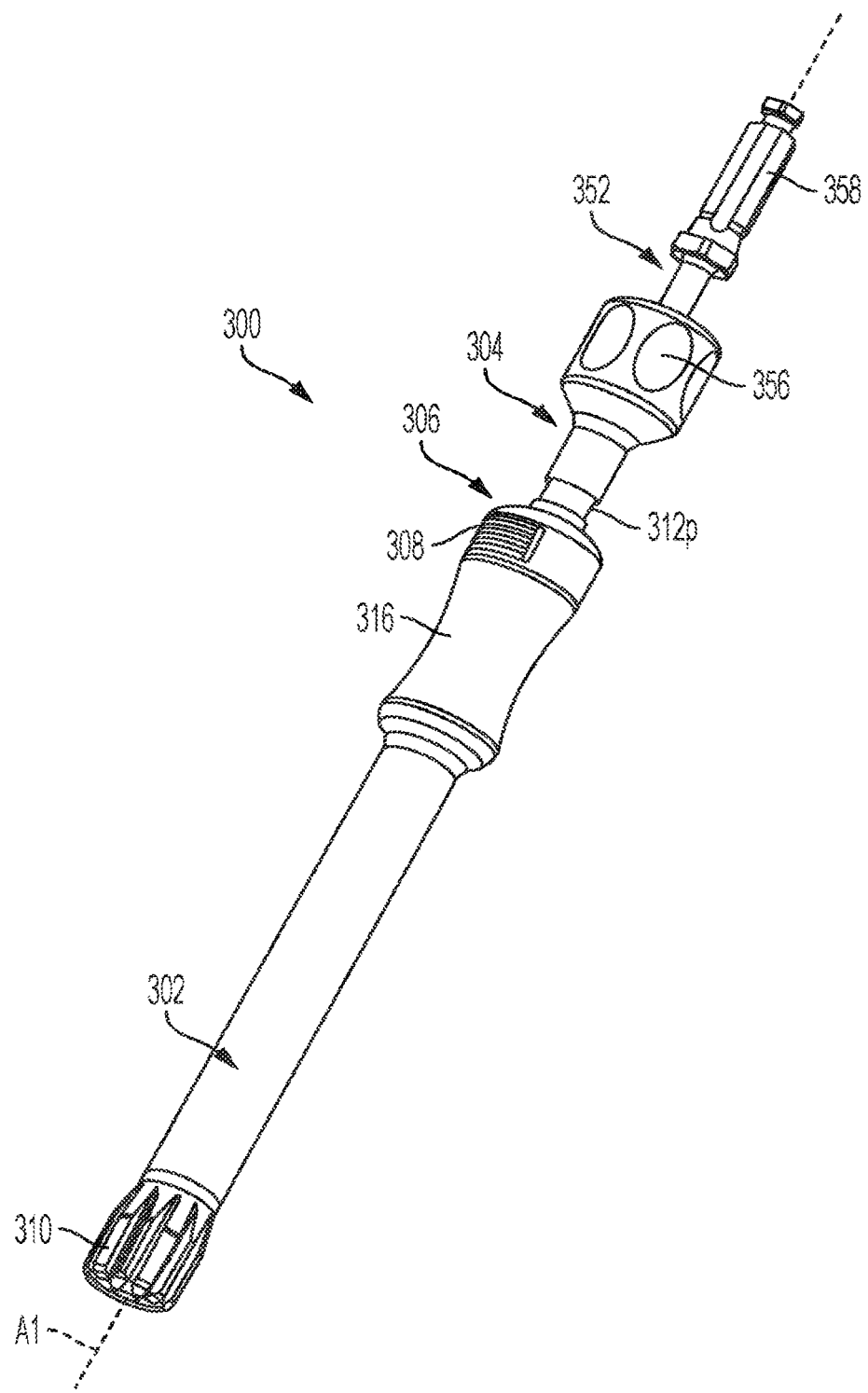
FIG. 3A is a perspective view of a reamer instrument.
Figure 3B:
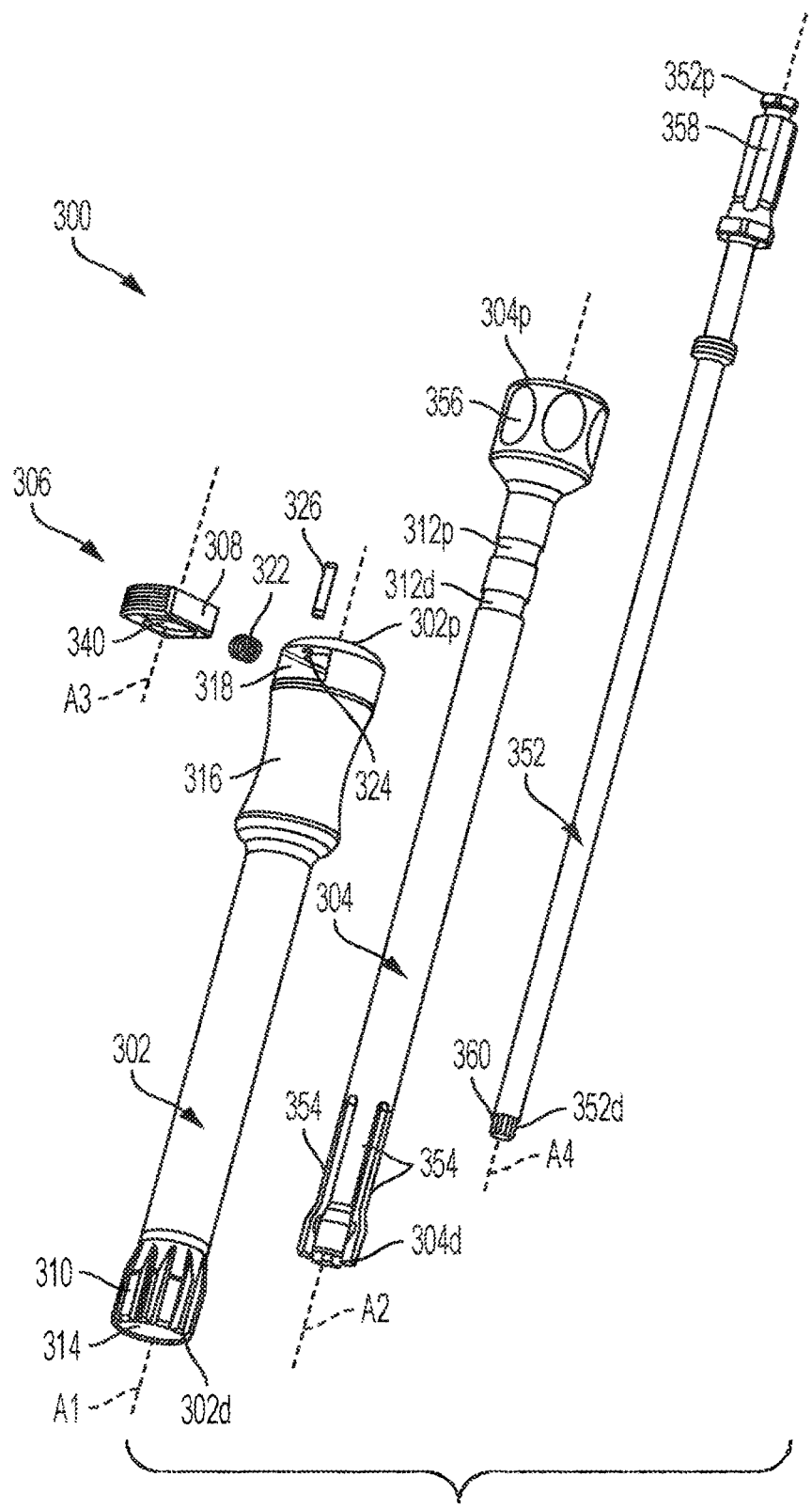
FIG. 3B is an exploded perspective view of the instrument of FIG. 3A.
Figure 3C:
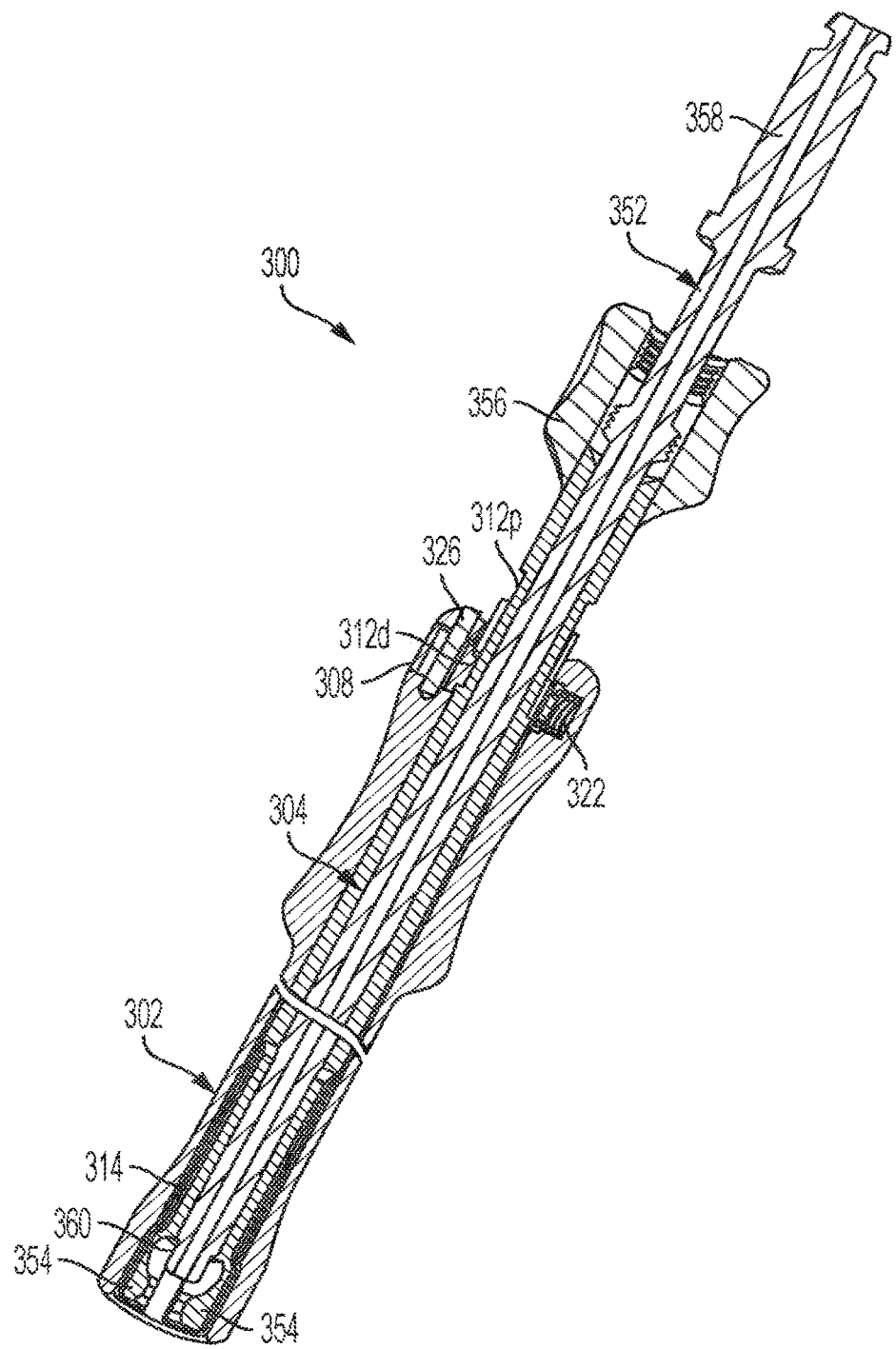
FIG. 3C is a sectional side view of the instrument of FIG. 3A.

The instrument can include features for integrating other steps of a procedure with the bone removal step. For example, the instrument can include features for grasping the bone anchor shank and can be used to deliver the shank to a target location within the patient. As another example, the instrument can include features for driving the bone anchor shank into the bone. FIGS. 3A-3C illustrate an exemplary instrument 300 having integrated grasping, driving, and reaming features. It will be appreciated that the instrument 300 can include any of the features described herein with respect to other disclosed instruments, e.g., the instrument 200.

As shown, the instrument 300 can include an outer shaft or reamer shaft 302, an inner shaft or grasper shaft 304, and a driver shaft 352. The instrument 300 can include a feedback mechanism 306 configured to notify a user that a threshold amount of reaming has occurred.

The outer shaft 302 can include an elongate, generally-cylindrical body having a proximal end 302$p$ and a distal end 302$d$ and extending along a central longitudinal axis A1. The outer shaft 302 can define a central passage 314 extending between the proximal and distal ends 302$p$, 302$d$. The inner shaft 304 and the driver shaft 352 can be coaxially received within the central passage 314, such that the central axis A1 of the outer shaft 302 is collinear with the central axis A2 of the inner shaft 304 and the central axis A4 of the driver shaft 352.

The distal end 302$d$ of the outer shaft 302 can include flutes 310 for removing bone. While a plurality of longitudinally extending flutes 310 are shown, it will be appreciated that any of a variety of bone removal features can be used instead or in addition, including blades, teeth, roughened surfaces, and the like. Various flute arrangements and configurations that can be used with the instrument 300 are described below. The flutes or other cutting features 310 can be treated with a coating, including hard coatings such as titanium nitride, to increase the durability and usable life of the instrument 300. The number of flutes 310 can vary, e.g., depending on the diameter of the instrument 300 or the diameter of hole to be reamed.

The outer shaft 302 can include features to facilitate grasping and manipulating the outer shaft. For example the outer shaft 302 can include a proximal handle 316. The handle 316 can be formed integrally with the outer shaft 302, as shown, or can be a separate component mated to the outer shaft. An outer surface of the handle 316 can be textured, faceted, knurled, grooved, etc. to facilitate gripping of the handle. The handle 316 can include a ratcheting mechanism, which can improve efficiency and reduce user fatigue. The outer shaft 302 can include a modular coupling to facilitate attachment of any of a variety of handle types or sizes thereto. Exemplary handle types can include T-shaped handles, pencil grip handles, pistol grip handles, knob-shaped handles, and so forth.

The outer shaft 302 can define a cavity 318 for housing the feedback mechanism 306. The cavity 318 can be formed in an enlarged diameter proximal portion of the outer shaft 302 as shown. The cavity 318 can be open to a sidewall of the outer shaft 302 and can intersect with the central passage 314. The cavity 318 can be sized and shaped to substantially correspond to the size and shape of an indicator 308 of the feedback mechanism 306. The indicator 308 can be slidably received within the cavity 318 such that the indicator can move within the cavity towards and away from the central passage 314, e.g., in a direction perpendicular to the axis A1. The floor of the cavity 318 can include a first bore in which at least a portion of an indicator spring 322 of the feedback mechanism 306 can be received. The outer shaft 302 can include an opening 324 formed in an endwall of the outer shaft that intersects with the cavity 318. The opening 324 can extend parallel to the axis A1 as shown. The opening 324 can be configured to receive at least a portion of a retention pin 326 of the feedback mechanism 306 therein.

The inner shaft 304 can include an elongate, generally-cylindrical body having a proximal end 304$p$ and a distal end 304$d$ and extending along a central longitudinal axis A2. The body of the shaft 304 can be solid or can be cannulated, e.g., to allow passage of the driver shaft 352 therethrough, to receive a guidewire, or to allow vacuum suction to be applied therethrough.

The distal end 304d of the inner shaft 304 can include features for grasping the head of a shank, e.g., to facilitate introduction of the shank into a patient using the instrument 300. For example, the inner shaft 304 can include a plurality of flexible and resilient fingers 354 extending distally therefrom. The inward-facing surfaces of the fingers 354 can have a geometry configured to capture and retain the head of a shank therein. The fingers 354 can have a geometry that is complementary to that of a bone anchor shank with which the instrument 300 is to be used. The inner surfaces of the fingers 354 can form a negative of the outer surface of the head of the shank. The inner surfaces of the fingers 354 can define a spherical pocket. The inner surfaces of the fingers 354 can include projections that extend radially-inward therefrom to contact a neck of the shank when a head of the shank is received between the fingers. In use, the fingers 354 can be flexed radially outward to allow insertion and removal of a shank head therefrom.

The inner shaft 304 can include one or more reliefs 312 for receiving at least a portion of the indicator 308. For example, the shaft 304 can include a first, proximal relief 312p configured to receive the indicator 308 to maintain the outer shaft 302 in a withdrawn position relative to the inner shaft 304, e.g., during initial insertion and driving of the bone anchor when no reaming is to be performed. The shaft 304 can include a second, distal relief 312d configured to receive the indicator 308, e.g., when a predetermined threshold displacement of the inner shaft relative to the outer shaft 302 is reached during a reaming operation. The reliefs 312 can be defined by a groove or slot formed in an outer surface of the inner shaft 304. The position of the distal relief 312d along the length of the inner shaft 304 can be selected to define the displacement threshold at which the feedback mechanism 306 is triggered. Moving the distal relief 312d closer to the distal end 304d of the inner shaft 304 can cause the feedback mechanism 306 to trigger later, resulting in more bone removal before triggering. Moving the distal relief 312d closer to the proximal end 304p of the inner shaft 304 can cause the feedback mechanism 306 to trigger earlier, resulting in less bone removal before triggering. It will be appreciated that the position of the distal relief 312d along the inner shaft 304 can be calibrated to the clearance space needed to assemble a bone anchor with which the instrument 300 is to be used.

The proximal end 304p of the inner shaft 304 can include features to facilitate grasping and manipulating the inner shaft. For example the inner shaft 304 can include a proximal handle 356. The handle 356 can be formed integrally with the inner shaft 304, as shown, or can be a separate component mated to the inner shaft. An outer surface of the handle 356 can be textured, faceted, knurled, grooved, etc. to facilitate gripping of the handle. The handle 356 can include a ratcheting mechanism, which can improve efficiency and reduce user fatigue. The inner shaft 304 can include a modular coupling to facilitate attachment of any of a variety of handle types or sizes thereto. Exemplary handle types can include T-shaped handles, pencil grip handles, pistol grip handles, knob-shaped handles, and so forth. The handle 356 of the inner shaft 304 can include an internal thread configured to mate with an external thread of a driver shaft 352.

The driver shaft 352 can include an elongate, generally-cylindrical body having a proximal end 352p and a distal end 352d and extending along a central longitudinal axis A4. The body of the driver shaft 352 can be solid or can be cannulated to allow passage of a guidewire therethrough.

The proximal end 352p of the driver shaft 352 can include a modular coupling 358 for selectively attaching the driver shaft to a structure or device for applying a rotational force to the driver shaft about the longitudinal axis A4. For example, the modular coupling 358 can be configured to attach the driver shaft 352 to a handle or knob configured to be grasped by a user, to a powered device such as an electric or pneumatic drill or driver, or to a surgical robot. In other embodiments, the driver shaft 352 can include a handle formed integrally therewith. Exemplary handles can include T-shaped handles, pencil grip handles, pistol grip handles, knob-shaped handles, and so forth.

The distal end 352d of the driver shaft 352 can include an drive tip 360 for engaging a corresponding drive interface of a bone anchor shank and for transferring rotational force applied to the driver shaft to the shank. Exemplary drive tips 360 can include Phillips, slotted, hexalobe, Torx®, hexagonal, pentalobe, and the like, of various standard or non-standard sizes. The drive tip 360 can also include a modular connector such that any of a plurality of drive tips having different types or sizes can be selectively coupled to the distal end of the driver shaft 352.

The feedback mechanism 306 can include an indicator 308 with a corresponding indicator spring 322 and a retention pin 326. The indicator 308 can include a substantially rectangular-parallelepiped body having proximal and distal abutment surfaces. A cylindrical opening 340 can be formed through the indicator 308, extending between the proximal and distal surfaces. The opening 340 can include a central longitudinal axis A3. The opening 340 can have a diameter or dimension that is greater than a maximum outer diameter or dimension of the inner shaft 304. Accordingly, when the central longitudinal axis A2 of the inner shaft 304 is coaxial with the central longitudinal axis A3 of the opening 340, the indicator 308 does not interfere with longitudinal translation of the inner shaft relative to the indicator and thus relative to the reamer shaft 302. As discussed further below, however, the indicator 308 can be positioned such that the axis A3 of the opening 340 is offset from the axis A2 of the inner shaft 304 and such that the indicator does interfere with longitudinal translation of the inner shaft relative thereto.

The indicator spring 322 can be partially received within the first bore formed in the bottom of the cavity 318 and partially received within a second bore formed in the sidewall of the indicator 308 that faces the bottom of the cavity. The indicator spring 322 can thus be effective to bias the indicator 308 away from the bottom of the cavity 318 such that the indicator is urged in a radially-outward direction. The retention pin 326 can extend through the opening 324 formed in the endwall of the outer shaft 302 and into an elongated slot formed in the indicator 308. The retention pin 326 can thus limit the travel of the indicator 308 within the cavity 318 to prevent the indicator from falling out of the instrument 300. The retention pin 326 can be welded or otherwise secured to the outer shaft 320 after assembly to prevent inadvertent disassembly.

The indicator 308 can be slidable within the cavity 318 between at least a first, released position and a second, engaged position. The indicator 308 can be biased towards the engaged position and can be configured to move from the engaged position to the released position when depressed by a user.

In the released or disengaged position, the axis A3 of the indicator opening 340 is aligned with the axis A2 of the inner shaft 304 such that longitudinal translation of the inner shaft is not limited by the indicator. Rather, the indicator 308 is moved out of the path of the inner shaft 304, such that the indicator does not restrict longitudinal movement of the inner shaft relative to the outer shaft 302. In this position, the inner shaft 304 is free to translate relative to the outer shaft 302 until one of the reliefs 312p, 312d is aligned with the indicator 308. The inner shaft 304 can have an outer diameter sufficient to maintain the indicator 308 in the disengaged position when neither of the reliefs 312p, 312d is aligned with the indicator. The indicator 308 can also be maintained in the disengaged position by manual user pressure applied to the indicator, e.g., when it is desired to ream bone beyond the threshold setting of the instrument 300 or to allow disassembly of the instrument.

In the engaged position, the bias of the indicator spring 322 urges the indicator 308 upwards such that a portion of the indicator is received within one of the reliefs 312p, 312d, preventing further longitudinal movement of the inner shaft 304 relative to the outer shaft 302.

While a single indicator 308 is shown, it will be appreciated that the instrument 300 can include any number of indicators, e.g., two or more. The indicator can be axially actuated instead of or in addition to being radially actuated as in the illustrated embodiment.

In use, the indicator 308 can be moved to the disengaged position and the reamer shaft 302 can be withdrawn proximally relative to the inner shaft 304 to position the indicator proximal to the proximal relief 312p. In this position, the grasping fingers 354 of the inner shaft 304 can be flexed radially-outward to load a bone anchor shank into the instrument 300. The driver shaft 352 can be advanced distally relative to the inner shaft 304 to insert the drive tip 360 of the driver shaft into a drive recess of the loaded bone anchor shank. The reamer shaft 302 can be advanced distally relative to the inner shaft 304 until the indicator 308 clicks into the proximal relief 312p of the inner shaft. In this position, the reaming flutes 310 can be spaced proximally from the bone surface and the reamer shaft 302 can at least partially cover the spring fingers 354 to prevent radially outward movement of the spring fingers, thereby preventing release of the bone anchor shank from the instrument 300. The tip of the bone anchor can be placed against the desired bone entry point or within a pre-tapped hole, and the driver shaft 352 can be rotated about the axis A4 to advance the shank into the bone. When it is desired to ream bone from around the implanted shank, the indicator 308 can be depressed to move the indicator to the disengaged position and allow the reamer shaft 302 to be advanced distally over the inner shaft 304. The reamer shaft 302 can be manipulated by the user as it is advanced further in the distal direction to remove bone from around the implanted shank. As the reamer shaft 302 is advanced distally, the shank of the bone anchor can axially displace the inner shaft 304 in a proximal direction relative to the reamer shaft. This can continue until the indicator 308 clicks into the distal relief 312d of the inner shaft 304, indicating to the user that a threshold amount of bone removal has occurred, e.g., via one or more of tactile, audible, and visual feedback.

It will be appreciated that the instrument 300 can be arranged in other ways to achieve a similar function. For example, the reamer shaft 302 can be withdrawn proximally relative to the inner shaft 304 to position the indicator 308 within the proximal relief 312p. In this position, the grasping fingers 354 of the inner shaft 304 can be flexed radially-outward to load a bone anchor shank into the instrument 300. The driver shaft 352 can be advanced distally relative to the inner shaft 304 to insert the drive tip 360 of the driver shaft into a drive recess of the loaded bone anchor shank. The indicator 308 can be moved to the disengaged position and the reamer shaft 302 can be advanced distally relative to the inner shaft 304 until the indicator 308 clicks into the distal relief 312d of the inner shaft. In this position, the reamer shaft 302 can at least partially cover the spring fingers 354 to prevent radially outward movement of the spring fingers, thereby preventing release of the bone anchor shank from the instrument 300. The tip of the bone anchor can be placed against the desired bone entry point or within a pre-tapped hole, and the driver shaft 352 can be rotated about the axis A4 to advance the shank into the bone. When it is desired to ream bone from around the implanted shank, the indicator 308 can be depressed to move the indicator to the disengaged position and allow the reamer shaft 302 to be advanced distally over the inner shaft 304. The reamer shaft 302 can be manipulated by the user as it is advanced further in the distal direction to remove bone from around the implanted shank. As the reamer shaft 302 is advanced distally, the shank of the bone anchor can axially displace the inner shaft 304 in a proximal direction relative to the reamer shaft. This can continue until the indicator 308 clicks into a third relief (not shown) disposed distal to the distal relief 312d of the inner shaft 304, indicating to the user that a threshold amount of bone removal has occurred, e.g., via one or more of tactile, audible, and visual feedback. The instrument 300 can include a bias element such as a coil spring or otherwise to bias the inner shaft 304 distally relative to the reamer shaft 302.

It will be appreciated that a number of variations on the instruments described herein are possible and within the scope of the present disclosure.

Figure 4:
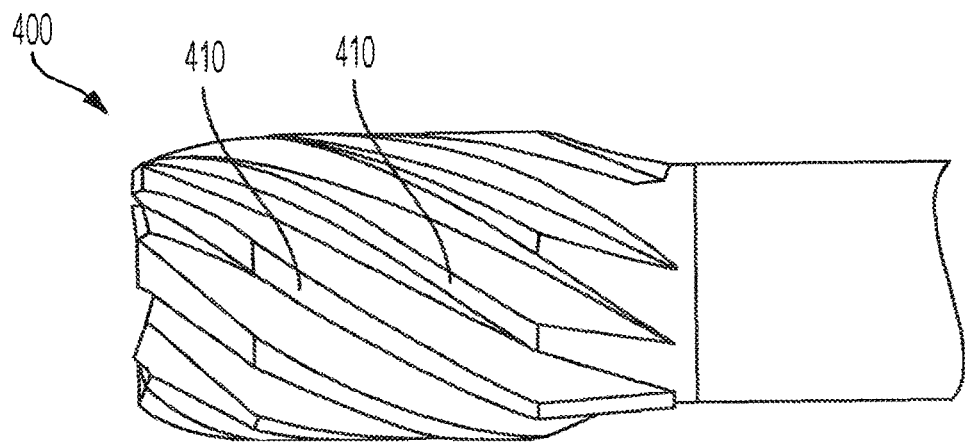
FIG. 4 is a side view of the distal end of an instrument having helical flutes.

Any of the instruments disclosed herein can include helical flutes. FIG. 4 illustrates an exemplary reamer instrument 400 having a plurality of helical flutes 410 formed on an outer surface thereof.

Figure 5A:
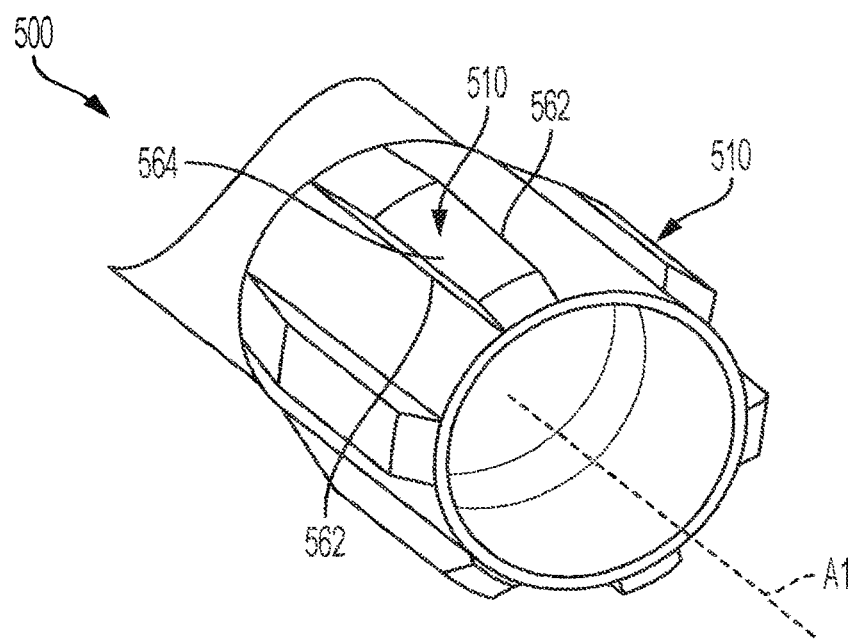
FIG. 5A is a perspective view of the distal end of an instrument having bi-directional flutes.
Figure 5B:
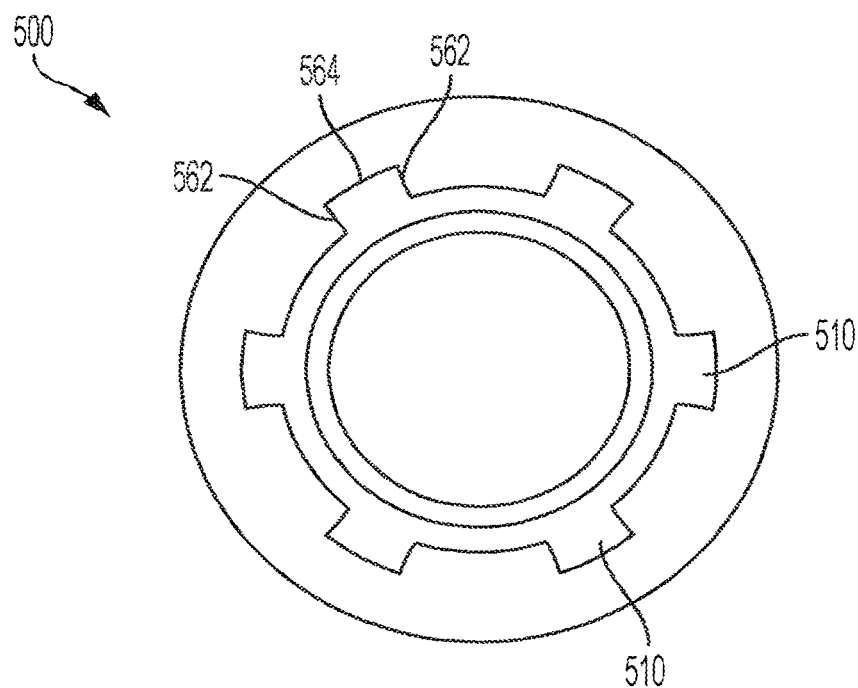
FIG. 5B is an end view of the instrument of FIG. 5A.
Figure 5C:
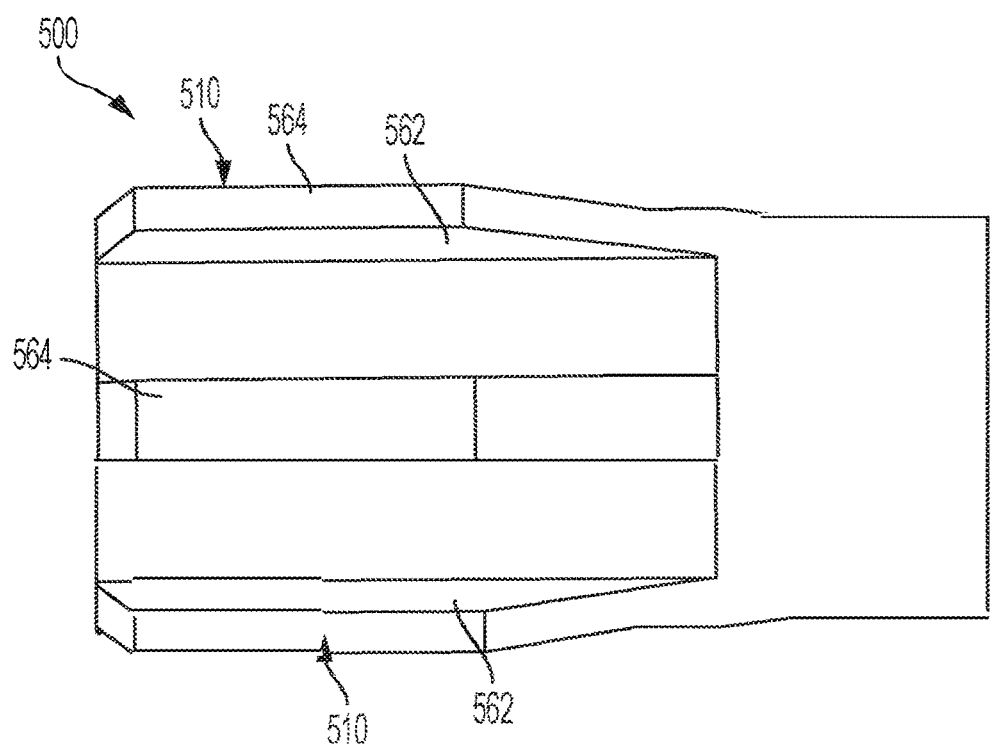
FIG. 5C is a side view of the distal end of the instrument of FIG. 5A.

Any of the instruments disclosed herein can include bi-direction flutes, e.g., flutes which are equally effective at cutting or otherwise removing bone when the reamer instrument is rotated clockwise as when the reamer instrument is rotated counterclockwise. FIGS. 5A-5C illustrate an exemplary reamer instrument 500 having a plurality of bi-directional flutes 510 formed on an outer surface thereof. As shown, the flutes 510 can be defined by opposed lateral surfaces 562 that extend radially-outward from the outer surface of the instrument 500 in a direction perpendicular or substantially perpendicular to the central longitudinal axis A1 of the instrument. The opposed lateral surfaces 562 can be connected by a planar or cylindrical outer surface 564. Proximal and distal ends of the flutes 510 can be ramped or tapered towards the nominal outer diameter of the instrument shaft.

Figure 6A:
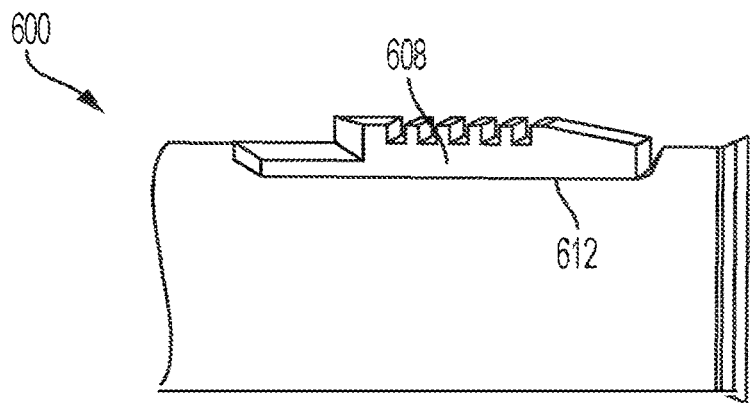
FIG. 6A is a side view of an instrument having a leaf-spring indicator feedback mechanism.
Figure 6B:
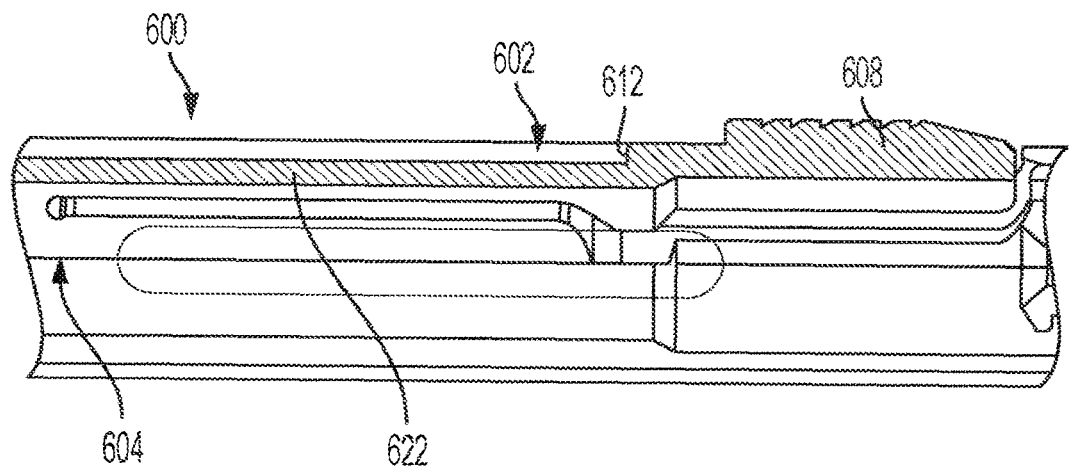
FIG. 6B is a sectional side view of the instrument of FIG. 6A.

Any of the instruments disclosed herein can include an indicator that is biased by a leaf spring, instead of or in addition to a coil spring. FIGS. 6A-6B illustrate an exemplary reamer instrument 600 having an indicator 608 defined at the free end of a cantilevered leaf spring 622. The leaf spring 622 can be formed by a section of the inner shaft 604. For example, as shown, a wire cut can be made in the sidewall of a hollow inner shaft 604 to define a cantilevered leaf spring portion 622. A raised indicator 608 can be formed at the free end of the leaf spring 622, such that the indicator protrudes from the outer surface of the inner shaft 604. In use, the instrument 600 can be initially configured with the indicator 608 deflected radially-inward by the inner sidewall of the outer shaft 602, flexing the leaf spring 622. When the inner shaft 604 is displaced proximally relative to the outer shaft 602 by a threshold amount, the indicator 608 can be aligned with an opening 612 formed in the outer shaft. The opening 612 can form a relief that allows the indicator 608 to move radially-outward under the bias of the spring 622, indicating to the user that the threshold amount of reaming has been completed.

Figure 7A:
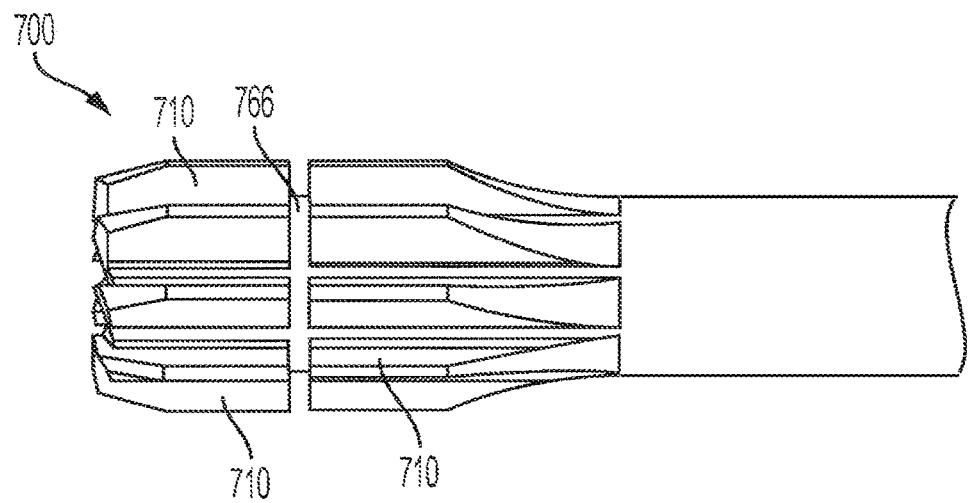
FIG. 7A is a side view of the distal end of an instrument having chip-breaker flutes.
Figure 7B:
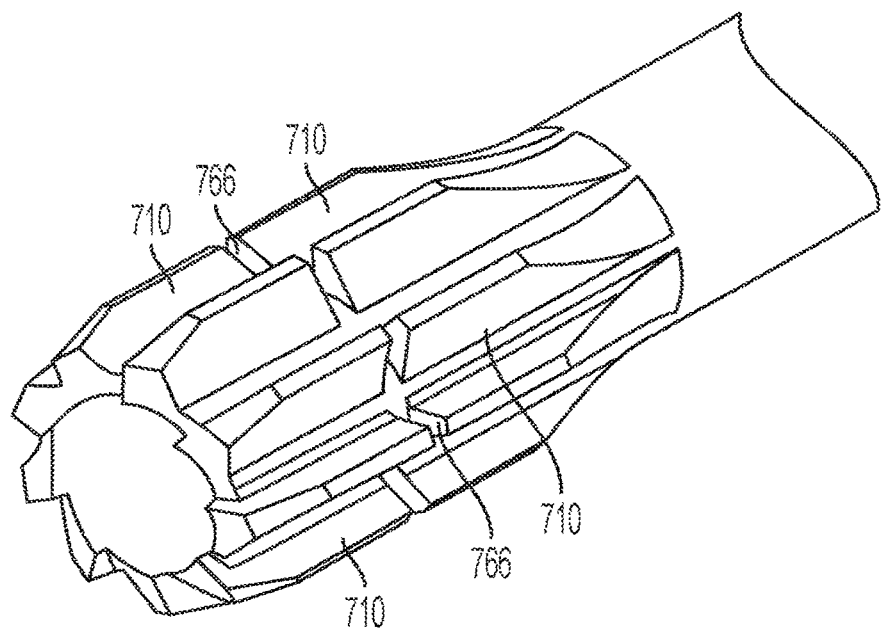
FIG. 7B is a perspective view of the distal end of the instrument of FIG. 7A.

Any of the instruments disclosed herein can include flutes configured to chip or break bone. FIGS. 7A-7B illustrate an exemplary reamer instrument 700 having a plurality of flutes 710 that are interrupted along their length by one or more radial grooves 766. The grooves 766 can be effective to chip or break off relatively large pieces of bone as the reamer 700 is manipulated with respect to the bone.

Figure 8:
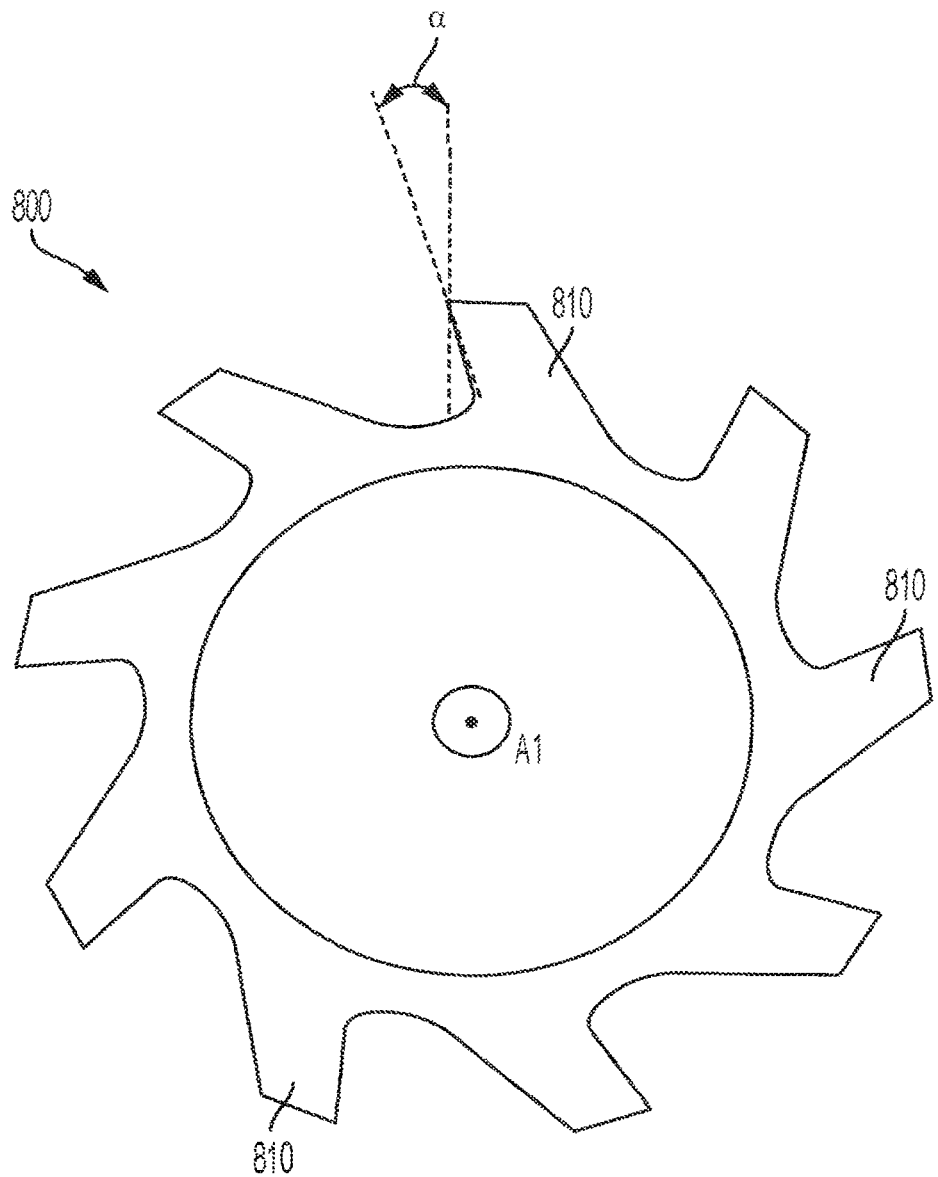
FIG. 8 is a sectional end view of an instrument having flutes with a non-zero rake angle.

Any of the instruments disclosed herein can include flutes having a rake angle of zero degrees. Any of the instruments disclosed herein can include flutes having a non-zero rake angle. In some embodiments, an instrument can include flutes having a rake angle in the range of about 0 degrees to about 10 degrees. A non-zero rake angle may be more effective at reaming harder bone, such as skull bone or long bones, with less user input force. FIG. 8 illustrates an exemplary reamer instrument 800 having flutes 810 with a non-zero rake angle α. The angle α can be defined between the leading edge of the flute 810 and a radial line perpendicular to the central longitudinal axis A1 of the instrument 800, when viewing a transverse cross section of the instrument.

Figure 9A:
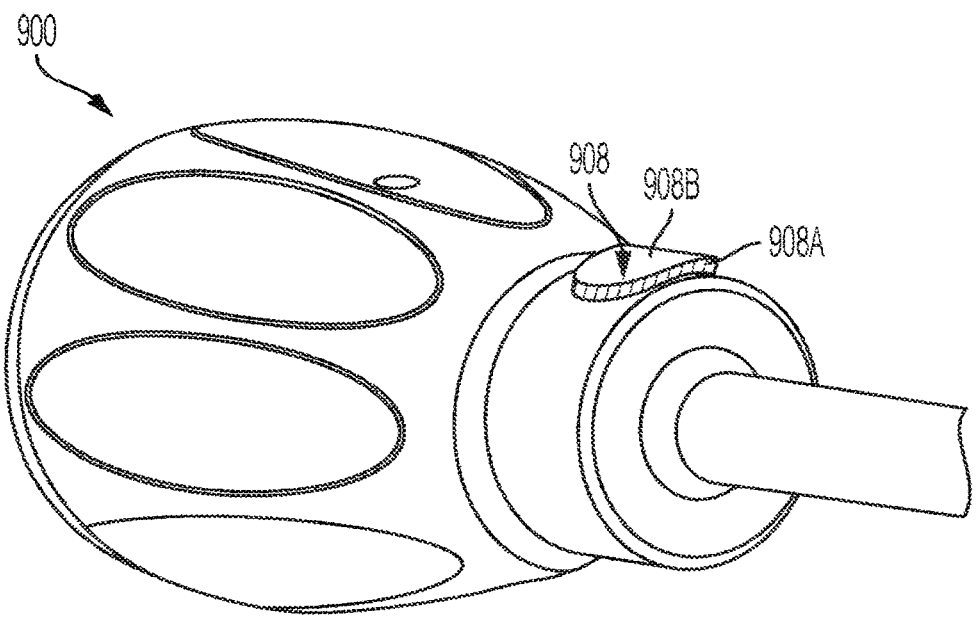
FIG. 9A is perspective view of the proximal end of an instrument having a visual feedback mechanism.

Any of the instruments disclosed herein can include a visual feedback mechanism as an alternative or in addition to the feedback mechanisms described herein. FIG. 9A illustrates an exemplary reamer instrument 900 in which the side surfaces 908A of the indicator 908 have a different color, texture, pattern, or the like as compared to the outer surface 908B of the indicator. This can allow the user to readily visually distinguish between the engaged and disengaged states of the indicator 908, and thus between the instrument 900 having not yet reached the threshold amount of reaming and the instrument having reached the threshold amount of reaming.

Figure 9B:
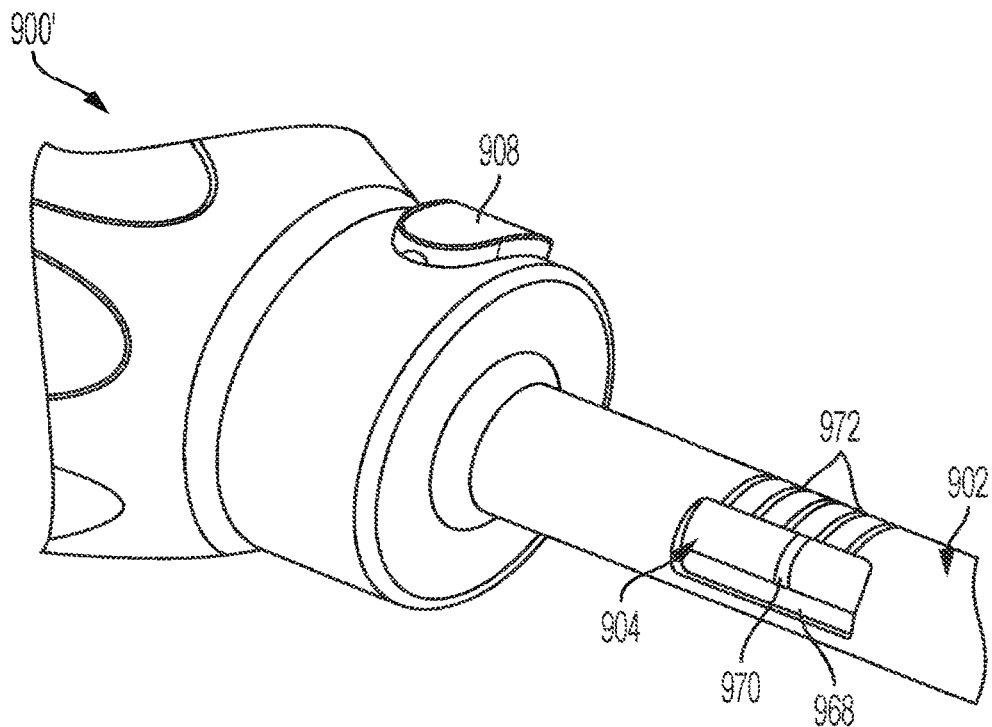
FIG. 9B is perspective view of the proximal end of an instrument having another visual feedback mechanism.

FIG. 9B illustrates an exemplary reamer instrument 900' in which the inner shaft 904 is visible through a window 968 formed in the outer shaft 902 in a proximal region of the instrument. The inner shaft 904 can include one or more indicator marks 970. The outer shaft 902 can include one or more markings 972 to define a scale indicative of the degree of reaming that has been completed. As more bone is reamed and the inner shaft 904 is displaced proximally relative to the outer shaft 902, the position of the indicator mark 970 along the scale 972 can change, giving the user a visual indication as to the degree of reaming. The user can observe the position of the indicator mark 970 relative to the scale 972 to assess the degree of reaming that has been completed.

FIGS. 10A-10D illustrate an exemplary embodiment of a reamer instrument 1000 that can be used, for example, for reaming bone to facilitate in situ assembly of a bone anchor. Except as indicated below and as will be readily appreciated by one having ordinary skill in the art in view of the present disclosure, the structure and operation of the instrument 1000 is substantially the same as that of the instrument 200 described above. Accordingly, a detailed description is omitted here for the sake of brevity. It will be appreciated that the instrument 1000 can include any of the features described herein with respect to other disclosed instruments, e.g., the instruments 200, 300.

As shown, the instrument 1000 can include an outer shaft 1002, an inner shaft 1004, and a feedback mechanism, e.g., in the form of one or more indicators 1008A, 1008B (e.g., spring loaded indicator 1008A, indicator cap 1008B, or other constructs capable of providing tactile, audible, and/or visual feedback to a user). The outer shaft 1002 can include flutes or other cutting features 1010 configured to remove bone when the outer shaft is manipulated relative to the bone. The inner shaft 1004 can be slidably mounted within the outer shaft 1002 and can be configured to trigger the feedback mechanism when sufficient bone removal has occurred. In particular, as the outer shaft 1002 is manipulated to remove bone surrounding an implanted bone anchor shank, the shank can displace the inner shaft 1004 proximally relative to the outer shaft. The degree of displacement of the inner shaft 1004 can correspond with the degree of bone removal. When displaced beyond a predetermined threshold distance, a relief 1012 formed in the inner shaft 1004 can be aligned with the first indicator 1008A, allowing movement of the first indicator to provide tactile, audible, and/or visual feedback to a user. A second indicator 1008B can move longitudinally with the inner shaft 1004, providing additional feedback to the user as to the degree of bone removal. For example, the degree to which the second indicator 1008B is recessed relative to, or protrudes from, the proximal end surface of the instrument 1000 can correspond with the degree of bone removal. The instrument 1000 can be configured such that the indicator 1008B is flush with, recessed below, or protrudes from the proximal end surface of the instrument when the degree of bone removal has reached a predetermined threshold amount, e.g., an amount necessary to assemble a modular bone anchor without interference.

The inner shaft 1004 can be retained within the central passage 1014 of the outer shaft 1002 by a retention element 1028. For example, the instrument 1000 can include a threaded end cap 1028 that mates with a threaded portion of the central passage 1014. A ring, clip, or other mating feature 1036 can be seated within counterpart grooves formed in the outer surface of the end cap 1028 and the inner surface of the central passage 1014. The mating feature 1036 can be radially-expandable and/or radially-collapsible. The mating feature 1036 can be a C-clip as shown, an O-ring, or various other structures. The mating feature 1036 can provide resistance to disassembly of the end cap 1028 from the outer shaft 1002. For example, before the end cap 1028 can be unthreaded from the outer shaft 1002, sufficient torque must be applied to the end cap to compress the C-clip 1036 out of a groove in which it is seated. This can help prevent inadvertent disassembly or loosening of the end cap 1028 during use of the instrument 1000. At least a portion of the outer surface of the end cap 1028 can form an outermost surface of the instrument 1000 and/or can be accessible to a user's grasp, which can allow the end cap to be assembled and disassembled by hand or without specialized tools. The end cap 1028 can include one or more flats or scalloped cuts 1074 to allow torque to be applied to the end cap, by hand or using a tool, e.g., to facilitate assembly and disassembly of the instrument 1000.

The instrument 1000 can include a bias element 1034 configured to bias the inner shaft 1004 distally relative to the outer shaft 1002. For example, the instrument 1000 can include a coil spring 1034 disposed coaxially over the inner shaft 1004. One end of the spring 1034 can bear against the distal end surface of the end cap 1028 and the opposite end of the spring can bear against an enlarged diameter portion of the inner shaft 1004, such that the spring urges the inner shaft in a distal direction relative to the outer shaft. While a distally biased inner shaft 1004 is shown, in other arrangements the inner shaft can be biased in a proximal direction.

The indicator 1008B can be operably coupled to the inner shaft 1004, e.g., at a proximal end 1004p of the inner shaft as shown. The indicator 1008B can be threaded onto the inner shaft 1004 or otherwise coupled thereto such that longitudinal movement of the inner shaft effects corresponding longitudinal movement of the indicator 1008B. The indicator 1008B can be slidably disposed within a lumen formed in the end cap 1028. The lumen can be open to an outer surface of the end cap 1028, e.g., a proximal end surface as shown. Accordingly, the longitudinal position of the indicator 1008B relative to the end cap 1028 can be assessed visually and/or tactilely by the user to determine the degree of reaming or bone removal that has occurred.

While two indicators 1008A, 1008B are shown, it will be appreciated that the instrument 1000 can include any number of indicators, e.g., one indicator or three or more. For example, the instrument can include only the proximal indicator 1008B. The indicator 1008B can be radially actuated instead of or in addition to being axially actuated as in the illustrated embodiment.

Figure 10A:
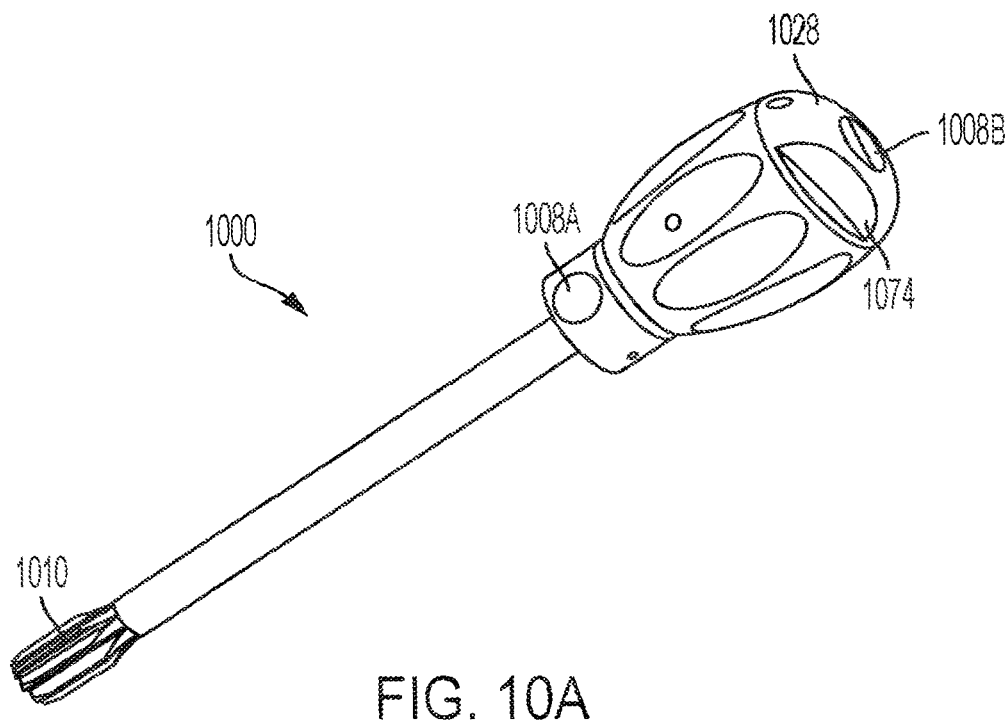
FIG. 10A is a perspective view of a reamer instrument.
Figure 10B:
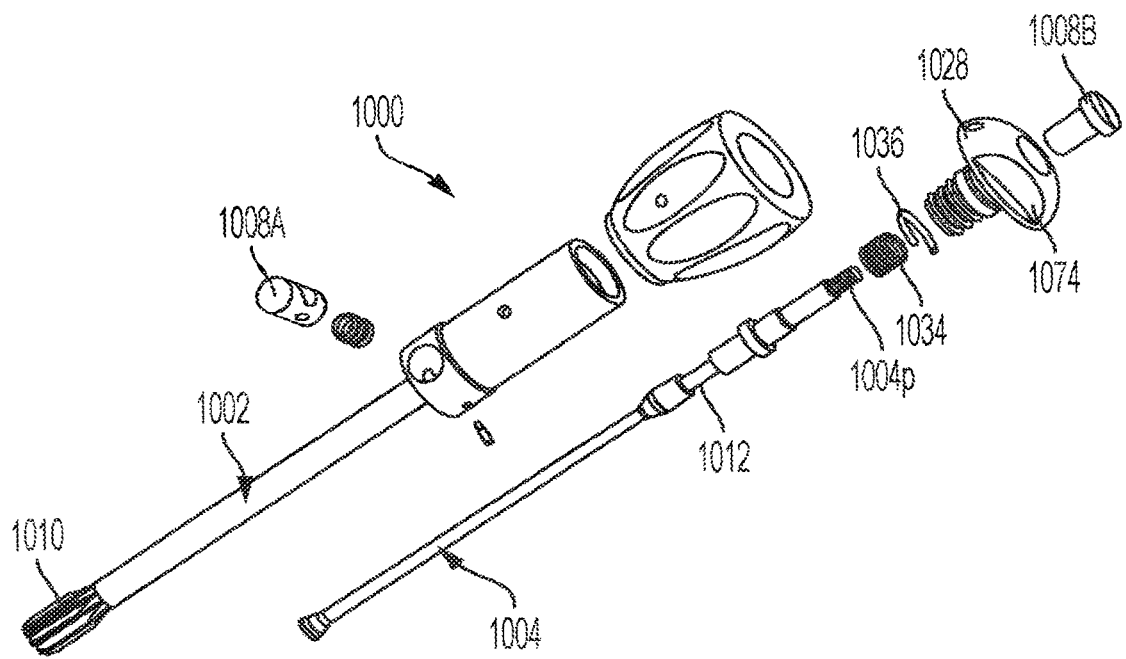
FIG. 10B is an exploded perspective view of the instrument of FIG. 10A.
Figure 10C:
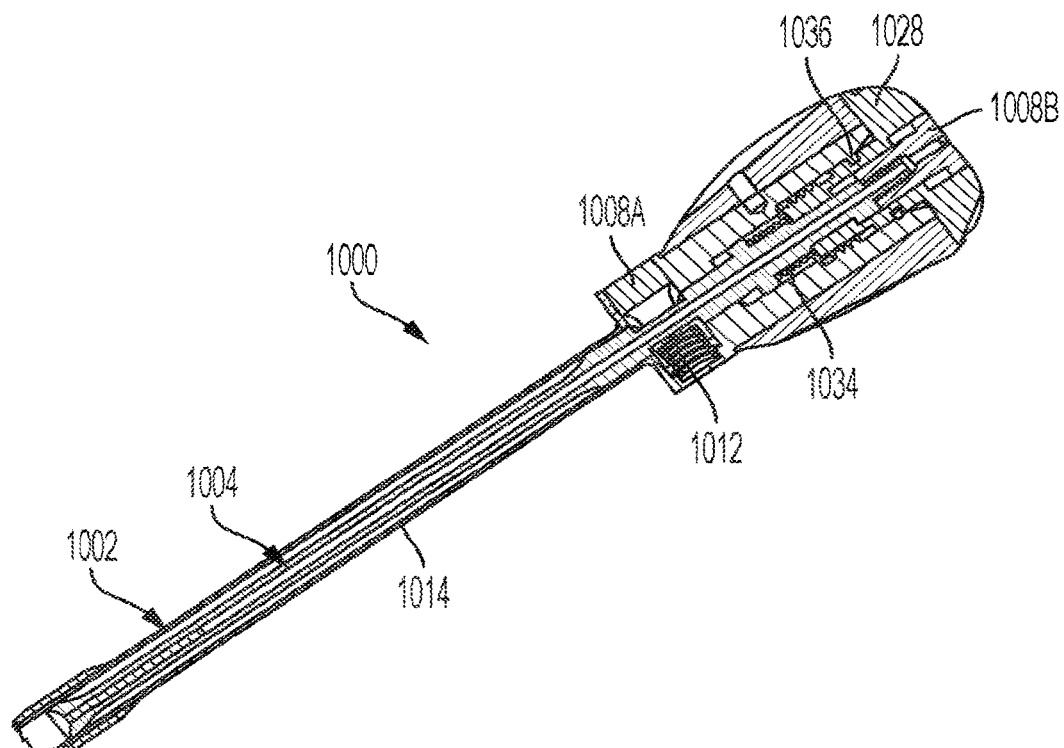
FIG. 10C is a sectional side view of the instrument of FIG. 10A.
Figure 10D:
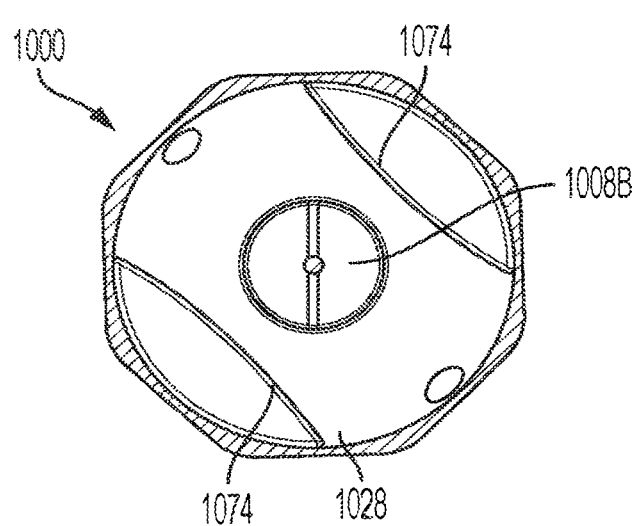
FIG. 10D is an end view of the instrument of FIG. 10A.

As shown in FIG. 10C, the body of the inner shaft 1004 can be cannulated, e.g., to allow passage of a guidewire therethrough or to allow vacuum suction to be applied therethrough. The instrument 1000 can be configured to receive a driver shaft therethrough. For example, the instrument 1000 can include a driver shaft inserted through a central cannulation of the inner shaft 1004. The driver shaft can be used, before or after reaming, to drive the shank of a bone anchor into the bone. The instrument 1000 can include tissue or bone collection features of the type described herein.

In use, the shank of a bone anchor can be driven into a bone. The reamer instrument 1000 can then be positioned over the implanted bone anchor shank to remove surrounding bone in preparation for assembly of a receiver member to the shank. In particular, the head of the shank can be inserted into the open distal end of the outer shaft 1002. The instrument 1000 can be manipulated relative to the shank to remove bone from around the shank. For example, the outer shaft 1002 can be rotated relative to the shank about the axis A1 and/or can be polyaxially articulated relative to the shank head. As bone is removed by the cutting flutes 1010, the outer shaft 1002 can move distally relative to the bone while the shank axially displaces the inner shaft 1004 in a proximal direction relative to the outer shaft. When the degree of proximal displacement is sufficient to align the relief 1012 with the indicator 1008A, the indicator 1008A can spring, snap, or click into the engaged position, thereby providing tactile, audible, and/or visual feedback to the user that a threshold amount of bone has been removed. The threshold amount can be an amount sufficient to ensure there is enough clearance to assemble a receiver member to the implanted shank. Proximal displacement of the inner shaft 1004 can also be effective to change the relative position between the indicator 1008B and the end cap 1028, providing further indication to the user as to the degree of bone removal. The instrument 1000 can be configured such that placement of the indicator 1008B in a position that is flush with, recessed below, or protruding from the proximal end surface of the end cap 1028 indicates that sufficient bone removal has occurred. The instrument 1000 can be separated from the shank and removed from the patient, and a receiver member can be attached to the shank using known techniques. The assembled bone anchor can be used to secure a rod or other fixation element to the bone of the patient.

In some embodiments, one or more of the feedback mechanisms of the embodiments of reamer instruments disclosed herein can be incorporated into other instruments without cutting or reaming elements. For example, FIGS. 11A-11F illustrate an exemplary embodiment of a clearance test instrument 1100 that can be used for testing or checking whether there is sufficient clearance surrounding an implanted shank to facilitate in situ assembly of a bone anchor. The clearance test instrument 1100 can be used by surgeons or other users to determine whether there is room to accommodate placement of a head or receiver member (e.g., 104 of FIG. 1) of the bone anchor on an implanted shank without interference from the surrounding boney anatomy.

Except as indicated below and as will be readily appreciated by one having ordinary skill in the art in view of the present disclosure, the structure and operation of the clearance test instrument 1100 is substantially the same as that of the instrument 200 and 1000 described above. Accordingly, a detailed description is omitted here for the sake of brevity. It will be appreciated that the clearance test instrument 1100 can include any of the features described herein with respect to other disclosed instruments, e.g., the instruments 200, 300, and/or 1000.

As shown, the clearance test instrument 1100 can include an outer shaft 1102, an inner shaft 1104, and a feedback mechanism, e.g., in the form of one or more indicators 1108 (e.g., a spring loaded indicator 1108A, an indicator cap 1108B, or other constructs capable of providing tactile, audible, and/or visual feedback to a user).

The outer shaft 1102 can include an elongate, generally cylindrical body having a proximal end 1102p and a distal end 1102d and extend along a central longitudinal axis A1. The outer shaft 1102 can define a central passage 1114 extending between the proximal and distal ends 1102p, 1102d. The distal end 1102d of the outer shaft can be sized and shaped to substantially correspond to the outer dimensions of a head of a bone anchor receiver member (e.g., 104) and thereby serve as a "trial head." For example, in some embodiments, the outer surface of the distal end 1102d can be sized and shaped to match or exceed one or more dimensions of the receiver head of a bone anchor (e.g., length, width, height, volume, and/or diameter). An opening 1103 can be defined at the distal end 1102d to receive the head of an implanted shank (e.g., 108).

The inner shaft 1104 can include an elongate, generally cylindrical body having a proximal end 1104p and a distal end 1104d. The inner shaft 1104 can be slidably mounted within the central passage 1114 of the outer shaft 1102, such that a central axis A2 of the inner shaft 1104 is collinear with the central axis A1 of the outer shaft 1102. The distal end 1104d of the inner shaft 1104 can include a bearing surface 1130 configured to contact and bear against the head of a shank implanted in bone as the clearance test instrument 1100 is moved distally over the shank. The bearing surface 1130 can have a geometry that is complementary to that of a bone anchor shank with which the instrument 1100 is to be used. For example, the bearing surface 1130 can form a negative of the outer surface of the head of the shank. As another example, the bearing surface 1130 can have a concave spherical shape. The bearing surface 1130 can be configured to slide across the proximal surface of the shank, e.g., as the instrument 1100 is rotated relative to the shank and/or as the instrument is polyaxially articulated relative to the shank.

The inner shaft 1104 can be retained within the central passage 1114 of the outer shaft 1002 by a retention element

1128. For example, the instrument 1100 can include a threaded end cap 1128 that mates with a threaded portion of the central passage 1114. A ring, clip, or other mating feature 1136 can be seated within counterpart grooves formed in the outer surface of the end cap 1128 and the inner surface of the central passage 1114. The mating feature 1136 can be radially-expandable and/or radially-collapsible. The mating feature 1136 can be a C-clip as shown, an O-ring, or various other structures.

The instrument 1100 can include a bias element 1134 configured to bias the inner shaft 1104 distally relative to the outer shaft 1102. For example, the instrument 1100 can include a coil spring 1134 disposed coaxially over the inner shaft 1104. One end of the spring 1134 can bear against the distal end surface of the end cap 1128 and the opposite end of the spring can bear against an enlarged diameter portion 1138 (e.g., a flange, etc.) of the inner shaft 1104, such that the spring urges the inner shaft in a distal direction relative to the outer shaft. While a distally biased inner shaft 1104 is shown, other arrangements are possible to achieve a similar effect.

The inner shaft 1104 can be configured to trigger the feedback mechanism when there is sufficient clearance surrounding an implanted shank. For example, in some embodiments, as the outer shaft 1102 is moved distally over the shank, the head of the shank can be received through the opening 1103 of the outer shaft 1102 and enter the central passage 1114. The shank can continue to progress into the central passage 1114 of the outer shaft 1102 until the outer shaft abuts bone, and thereby prevents further distal movement of the outer shaft. As the shank progresses into the central passage 1114 of the outer shaft 1102, the shank can displace the inner shaft 1104 proximally relative to the outer shaft and the indicator 1108A. When the inner shaft 1104 is axially displaced relative to the outer shaft 1102, an enlarged diameter portion 1113 of the inner shaft 1104 can translate relative to the indicator 1108A by moving through a through-hole formed in the indicator 1108A in which the inner shaft 1104 is disposed. When the inner shaft 1104 is axially displaced beyond a predetermined threshold distance, the indicator 1108A can come out of alignment with the enlarged diameter portion 1113 of the inner shaft 1104 and into alignment with a relief 1112 formed in the inner shaft 1104. The relief 1112 can have a reduced diameter relative to the enlarged diameter portion 1113 and the through-hole formed in the indicator 1108A such that the indicator can move radially relative to the inner shaft 1104 when the indicator is aligned with the relief 1112. The instrument can further include a biasing element 1122 (e.g., spring) to bias the indicator 1108A radially, such that the indicator 1108A will move radially outward when aligned with the relief 1112. This movement allows the indicator 1108A to provide tactile, audible, and/or visual feedback to a user (e.g., in a manner substantially the same as the spring loaded indicator 208 of FIG. 2). The position of the relief 1112 along the length of the inner shaft 1104 can be selected to define the displacement threshold at which the spring loaded indicator 1108A is triggered. It will be appreciated that the position of the relief 1112 along the inner shaft 1104 can be calibrated to the clearance space needed to assemble a bone anchor with which the instrument 1100 is to be used.

Alternatively or additionally, in some embodiments, a second indicator 1108B (e.g., an indicator cap) can be operably coupled to the inner shaft 1104, e.g., at a proximal end 1104p of the inner shaft as shown. The indicator 1108B can be threaded onto the inner shaft 1104 or otherwise coupled thereto such that longitudinal movement of the inner shaft effects corresponding longitudinal movement of the indicator 1108B. The indicator 1108B can be slidably disposed within a lumen formed in the end cap 1128. The lumen can be open to an outer surface of the end cap 1128, e.g., at a proximal end surface as shown. Accordingly, the longitudinal position of the indicator 1108B relative to the end cap 1128 can be assessed visually and/or tactilely by the user to determine the degree of clearance surrounding the head of the shank. For example, the degree to which the indicator 1108B is recessed relative to, or protrudes from, the proximal end surface of the instrument 1100 can correspond with the degree of clearance. In some embodiments, the instrument 1100 can be configured such that the indicator 1108B is flush with or protrudes from the proximal end surface of the instrument when the degree of clearance has reached a predetermined threshold amount, e.g., an amount necessary to assemble a modular bone anchor without interference.

While two indicators 1108A, 1108B are shown, it will be appreciated that the instrument 1100 can include any number of indicators, e.g., one, three, or more. For example, the instrument can include only the distal indicator 1108A or only the proximal indicator 1108B. Further, the indicator 1108B can be radially actuated instead of or in addition to being axially actuated as in the illustrated embodiment.

The outer shaft 1102 can include features to facilitate grasping and manipulating the outer shaft. For example the outer shaft 1102 can include a proximal handle 1116. The handle 1116 can be formed integrally with the outer shaft 1102 or, as shown, can be a separate component mated to the outer shaft. The handle 1116 can define a lumen in which at least a portion of the outer shaft 1102 is received, and can be secured thereto using a cross-pin or other attachment feature. In some embodiments, the handle 1116 can be overmolded on the outer shaft 1102, e.g., a silicone handle overmolded on the shaft 1102. An outer surface of the handle 1116 can be textured, faceted, knurled, grooved, etc. to facilitate gripping of the handle. The outer shaft 1102 can include a modular coupling to facilitate attachment of any of a variety of handle types or sizes thereto. Exemplary handle types can include T-shaped handles, pencil grip handles, pistol grip handles, knob-shaped handles, and so forth.

Figure 11A:
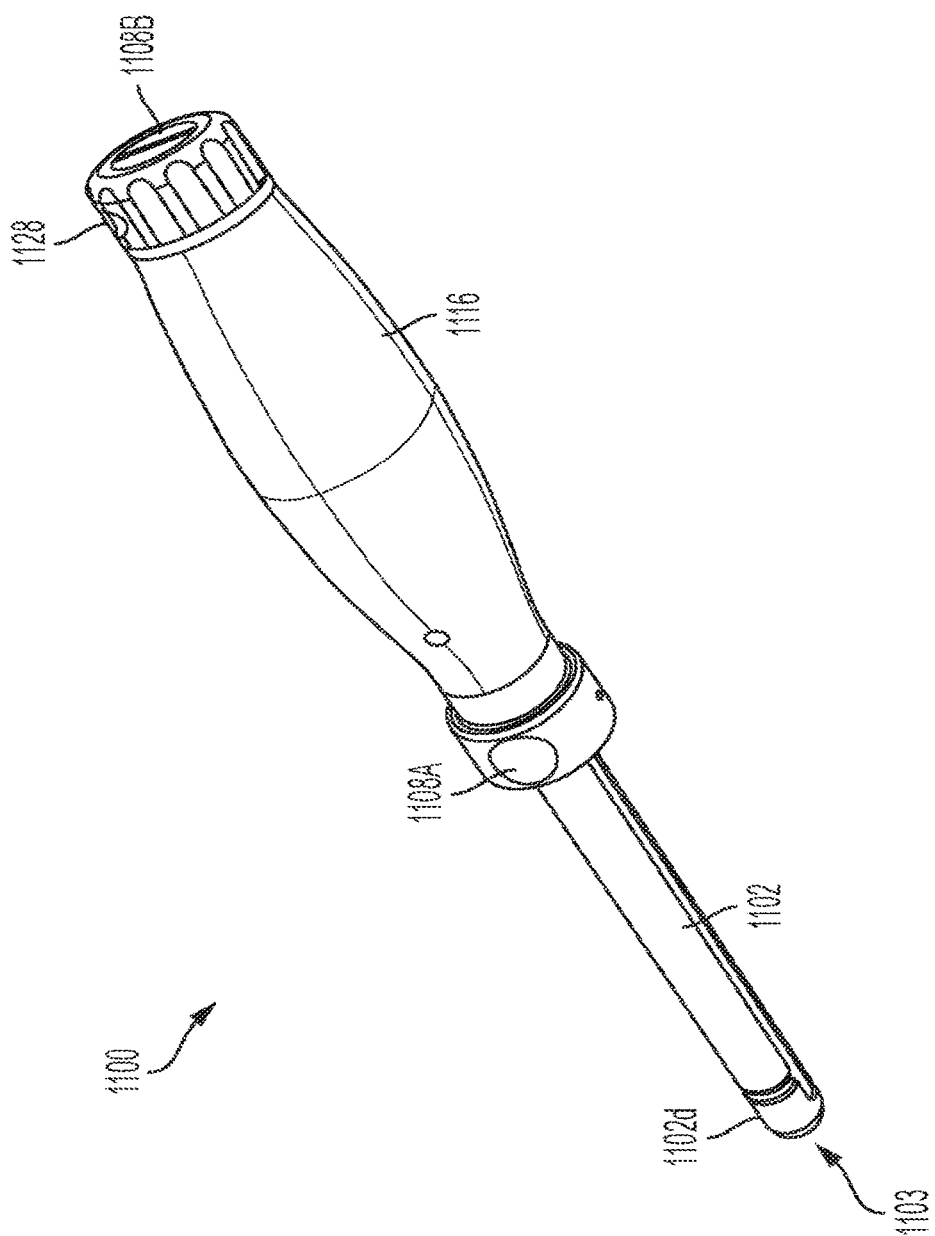
FIG. 11A is a perspective view of one embodiment of a clearance test instrument.
Figure 11B:
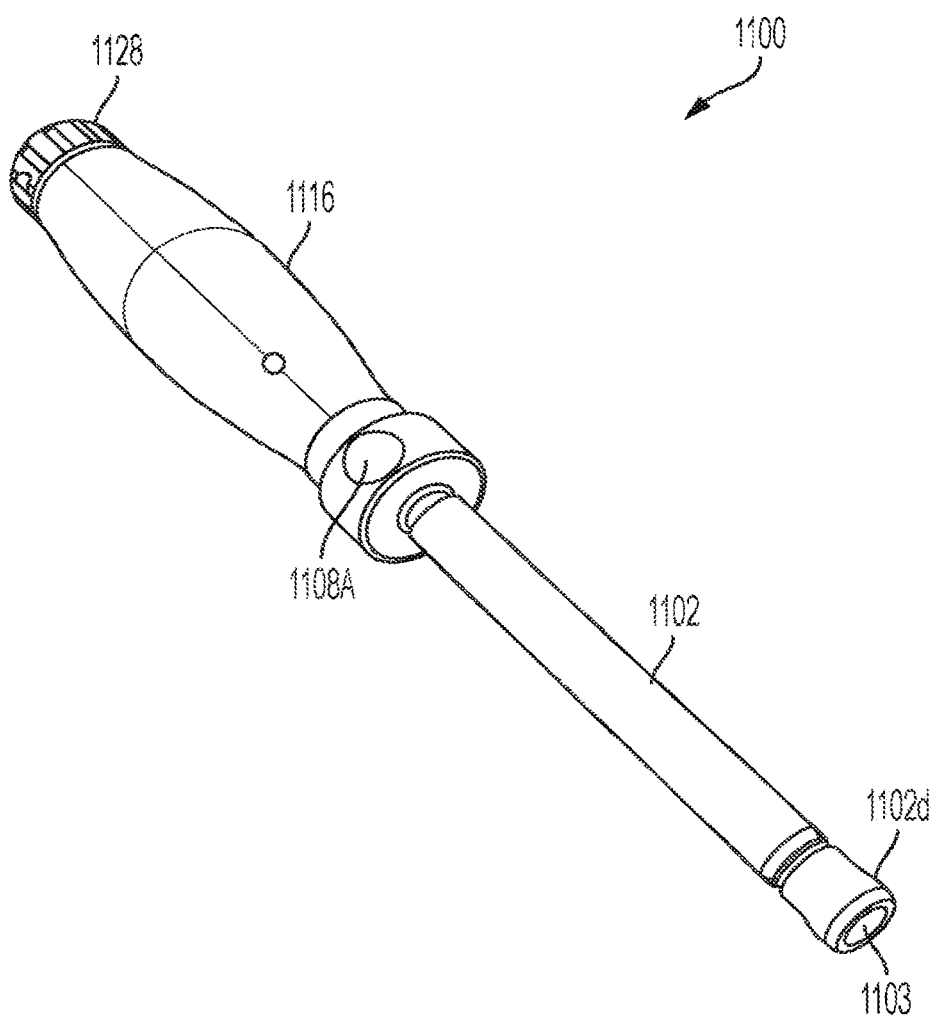
FIG. 11B is another perspective view of the instrument of FIG. 11A.
Figure 11C:
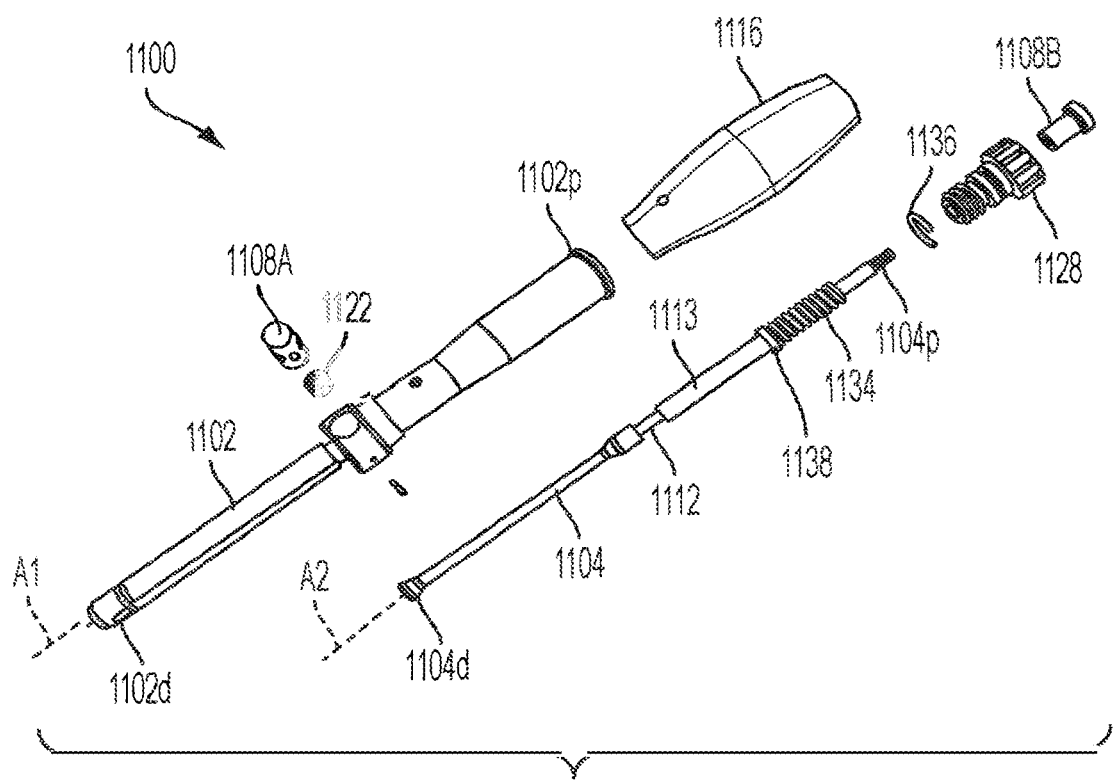
FIG. 11C is an exploded view of the instrument of FIG. 11A.
Figure 11D:
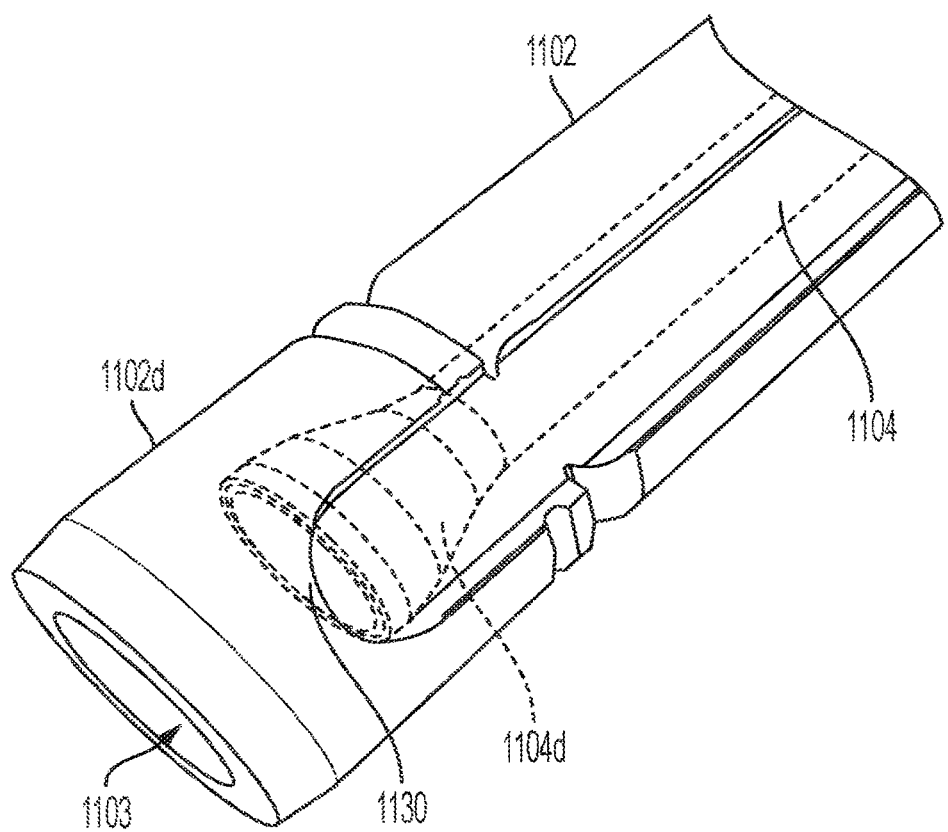
FIG. 11D is a partially-transparent perspective view of an inner shaft slidably mounted within an outer shaft of the instrument of FIG. 11A.
Figure 11E:
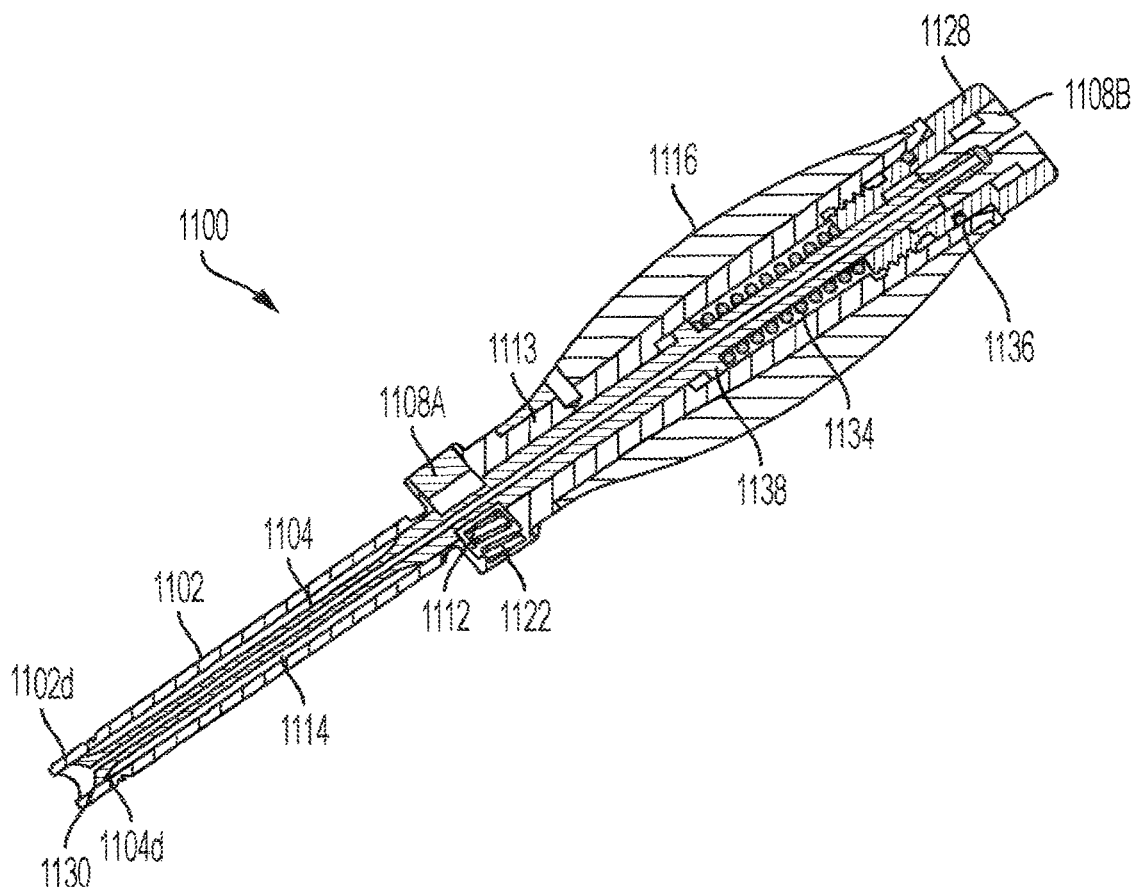
FIG. 11E is a side cross-sectional view of the instrument of FIG. 11A.
Figure 11F:
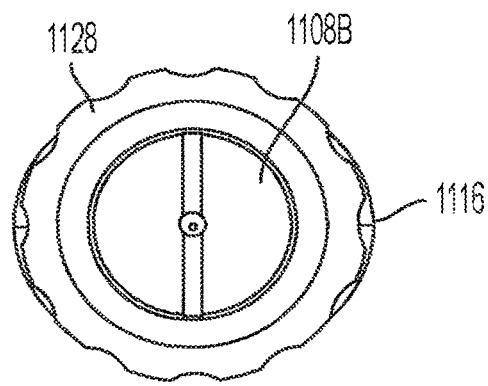
FIG. 11F is a proximal end view of the instrument of FIG. 11A.

As shown in FIG. 11D, the body of the inner shaft 1104 can be cannulated, e.g., to allow the instrument 1100 to be passed over a guidewire during use or to allow vacuum suction to be applied therethrough. In embodiments where a guidewire is employed, it can serve as an aid or redundant method for mating the instrument 1100 with the head of a bone shank. In some embodiments, the instrument 1100 can be configured to receive a driver shaft therethrough. For example, the instrument 1100 can include a shaft large enough to accommodate a driver used to drive the shank of a bone anchor into the bone. The instrument 1100 can also include tissue or bone collection features of the type described herein.

In one embodiment of use, the shank of a bone anchor can be driven into a bone. The clearance test instrument 1100 can then be positioned over the implanted bone anchor shank to test or check whether there is sufficient clearance surrounding the shank prior to assembly of a receiver member to the shank. In particular, the head of the shank can be inserted into the opening 1103 at the distal end 1102d of the outer shaft 1102. The outer shaft 1102 can be moved distally until the distal end 1102d of the outer shaft abuts bone and thereby prevents further distal movement of the outer shaft. As the shank progresses into the central passage 1114 of the outer shaft 1102, the shank can displace the inner shaft 1104 in a proximal direction relative to the outer shaft. When the degree of proximal displacement is sufficient to align the relief 1112 with the indicator 1108A, the indicator 1108A can spring, snap, or click into the engaged position (e.g., from force applied by the biasing element 1122), thereby providing tactile, audible, and/or visual feedback to the user that a threshold amount of clearance has been achieved. The threshold amount of clearance can be an amount sufficient to assemble a receiver member to the implanted shank. Failure to trigger the spring loaded indicator 1108A can be an indication that there is not enough room to accommodate the head of the bone anchor and that additional reaming of the boney anatomy surrounding the shank may be needed or the bone screw may need to be backed out to increase the clearance.

Proximal displacement of the inner shaft 1104 can also be effective to change the relative position between the indicator 11008B and the end cap 1128, providing further indication to the user as to the degree of clearance surrounding the shank. The instrument 1100 can be configured such that placement of the indicator 1108B in a position that is flush with, or in a position that protrudes from, the proximal end surface of the end cap 1128 indicates that there is sufficient clearance for assembly of the bone anchor in situ. Following the test fit, the instrument 1100 can be separated from the shank and removed from the patient, and a receiver member can be attached to the shank using known techniques. The assembled bone anchor can be used to secure a rod or other fixation element to the bone of the patient.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

It will be appreciated from the foregoing that the instruments disclosed herein can provide tactile, audible, and/or visual feedback when the bone is reamed enough to allow the receiver to be attached. This can advantageously prevent over- or under-reaming of the bone. The instruments disclosed herein can advantageously reduce the number of instruments required for a particular procedure, and make the procedure less cumbersome and time-consuming by reducing or eliminating the need to switch between multiple instruments.

The instruments disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the instruments disclosed herein can be rigid or flexible. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of removing bone from around a bone anchor shank implanted in a bone such as the pedicle or lateral mass of a human spine, it will be appreciated that the methods and devices disclosed herein can be used with any human or animal bone, implant, non-bone anatomy, non-living object, and so forth.

Although specific embodiments are described above, it should be understood that numerous changes may be made within the spirit and scope of the concepts described.

The invention claimed is:

1. A surgical instrument, comprising:
   an outer shaft having a cutting element at a distal end thereof and a central passage extending proximally from the distal end;
   an inner shaft disposed within the central passage of the outer shaft, the inner shaft being configured to move longitudinally relative to the outer shaft as the cutting element is used to remove bone from around an implanted bone anchor shank; and
   an indicator configured to generate user feedback when the inner shaft moves longitudinally relative to the outer shaft by a threshold distance;
   wherein a distal end of the inner shaft includes a bearing surface configured to contact and slide across a proximal surface of the implanted bone anchor shank as the instrument is rotated axially and/or polyaxially articulated relative to the shank.

2. The instrument of claim 1, wherein the threshold distance corresponds with an amount of clearance space needed to assemble a receiver member to an implanted bone anchor shank.

3. The instrument of claim 1, further comprising a collection chamber in fluid communication with at least one of (a) a cannulation formed in the inner shaft and (b) a space defined between the inner and outer shafts, such that material removed by the instrument is collected in the chamber.

4. The instrument of claim 1, wherein the cutting element comprises a plurality of longitudinally-extending flutes spaced about an outer perimeter of the outer shaft.

5. The instrument of claim 4, wherein the flutes are at least one of (a) helical, (b) bi-directional, (c) interrupted along their length by one or more radial grooves, (d) have a non-zero rake angle, and (e) have distal-facing surfaces that are angled radially inwards.

6. The instrument of claim 1, further comprising a driver shaft inserted through the inner shaft and configured to apply torque to a bone anchor shank.

7. The instrument of claim 6, wherein the inner shaft includes a plurality of flexible and resilient fingers configured to grasp a head portion of a bone anchor shank.

8. A surgical method, comprising:
   driving a shank of a bone anchor into bone;
   positioning a reamer instrument over the implanted shank such that a cutting element at a distal end of an outer shaft of the reamer instrument at least partially surrounds the shank of the bone anchor and a distal end bearing surface of an inner shaft of the reamer instrument disposed within a central passage of the outer shaft contacts a proximal surface of the shank;
   manipulating the reamer instrument relative to the shank to remove bone from around the shank, the distal end bearing surface of the inner shaft of the reamer instrument sliding across the proximal surface of the shank as the instrument is rotated axially and/or polyaxially articulated relative to the shank;
   as bone is removed by the reamer instrument, advancing the outer shaft distally relative to the bone while the shank axially displaces the inner shaft in a proximal direction relative to the outer shaft; and generating feedback indicative of a degree of bone removal using an indicator configured to trigger when the inner shaft moves relative to the outer shaft by a threshold distance.

9. The method of claim 8, wherein said driving comprises rotating the shank relative to the bone using a driver shaft inserted through the inner shaft of the reamer instrument.

10. The method of claim 8, wherein said positioning comprises inserting a head portion of the shank into an open distal end of the outer shaft of the instrument.

11. The method of claim 8, wherein said manipulating comprises at least one of (a) rotating the outer shaft of the instrument relative to a head portion of the shank about a central longitudinal axis of the outer shaft and (b) polyaxially articulating the outer shaft of the instrument relative to the head portion of the shank.

12. The method of claim 8, wherein the threshold distance corresponds with an amount of bone removal sufficient to assemble a receiver member to the implanted shank.

13. The method of claim 8, further comprising separating the instrument from the shank and attaching a receiver member to the implanted shank.

14. The method of claim 8, further comprising retaining the shank to the instrument by grasping the head of the shank between a plurality of fingers of the inner shaft.

15. The instrument of claim 1, wherein the user feedback is at least one of audible, visual, and tactile feedback.

16. The instrument of claim 15, wherein the indicator need not be contacted to convey the user feedback.

17. The instrument of claim 1, wherein the indicator provides visual feedback.

18. The instrument of claim 17, wherein the indicator provides visual feedback in a form selected from the group consisting of color, texture, and pattern.

19. The method of claim 8, wherein the feedback generated by the indicator is at least one of audible, visual, and tactile feedback.

20. The instrument of claim 1, wherein the bearing surface forms a negative of the proximal surface of the implanted bone anchor shank.

21. The instrument of claim 1, wherein the bearing surface has a concave spherical shape.

22. The instrument of claim 1, wherein the inner shaft is biased distally relative to the outer shaft.

23. The instrument of claim 1, further comprising one or more stops to limit longitudinal movement of the inner shaft relative to the outer shaft.

\* \* \* \* \*